(12) United States Patent
Ward et al.

(10) Patent No.: US 6,210,937 B1
(45) Date of Patent: Apr. 3, 2001

(54) DEVELOPMENT OF GENETICALLY ENGINEERED BACTERIA FOR PRODUCTION OF SELECTED AROMATIC COMPOUNDS

(75) Inventors: Thomas E. Ward; Carolyn S. Watkins, both of Idaho Falls, ID (US); Deborah K. Bulmer, Henderson, NV (US); Bruce F. Johnson, Scotia; Mohan Amaratunga, Clifton Park, both of NY (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/064,693

(22) Filed: Apr. 22, 1998

Related U.S. Application Data

(60) Provisional application No. 60/044,094, filed on Apr. 22, 1997.

(51) Int. Cl.⁷ .............................. C12P 7/42; C12N 1/21; C12N 15/63
(52) U.S. Cl. ................. 435/146; 435/232; 435/320.1; 435/252.3
(58) Field of Search .................... 435/146, 232, 435/320.1, 252.3

(56) References Cited

U.S. PATENT DOCUMENTS

| | | | |
|---|---|---|---|
| 4,621,153 | 11/1986 | Hatch | 562/443 |
| 4,681,852 | 7/1987 | Tribe | 435/108 |
| 5,008,190 | 4/1991 | Lee et al. | 435/108 |
| 5,030,567 | 7/1991 | Lee et al. | 435/108 |
| 5,168,056 | 12/1992 | Frost | 435/172.3 |
| 5,169,768 | 12/1992 | Backman | 435/108 |
| 5,272,073 | 12/1993 | Frost et al. | 435/155 |
| 5,409,830 | 4/1995 | Lim et al. | 435/252.8 |
| 5,487,987 | 1/1996 | Frost et al. | 435/142 |

FOREIGN PATENT DOCUMENTS

| | | |
|---|---|---|
| 0077196 A2 | 4/1983 | (EP) . |
| 8-107789 | 4/1996 | (JP) . |
| 87/00202 * | 1/1987 | (WO) . |
| WO 94/08015 | 4/1994 | (WO) . |
| WO 95/33843 | 12/1995 | (WO) . |
| 96/08567 * | 3/1996 | (WO) . |

OTHER PUBLICATIONS

M. Siebert et al., "Formation of 4–Hydroxybenzoate in *Escherichia coli:* Characterization of the ubiC Gene and Its Encoded Enzyme Chorismate–Pyruvate Lyase", Microbiology 140: 897–904, 1994.*

G. Gosset et al., "A Direct Comparison of Approches For Increasing Carbon Flow to Aromatic Biosynthesis in *Escherichia coli*" J. Indust. Microbiol. 17(1):47–52, Jul. 1996.*

* cited by examiner

*Primary Examiner*—Rebecca E. Prouty
(74) *Attorney, Agent, or Firm*—Clayton Howarth & Cannon

(57) ABSTRACT

The cloning and expression of genes in the common aromatic pathway of *E. coli* are described. A compound for which chorismate, the final product of the common aromatic pathway, is an anabolic intermediate can be produced by cloning and expressing selected genes of the common aromatic pathway and the genes coding for enzymes necessary to convert chorismate to the selected compound. Plasmids carrying selected genes of the common aromatic pathway are also described.

14 Claims, 1 Drawing Sheet

DEVELOPMENT OF GENETICALLY ENGINEERED BACTERIA FOR PRODUCTION OF SELECTED AROMATIC COMPOUNDS

RELATED APPLICATION

This application claims priority from provisional application Ser. No. 60/044,094 filed Apr. 22, 1997.

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND OF THE INVENTION

This invention relates to synthesis of aromatic compounds by the conversion of biomass-derived carbon sources. More particularly, the invention relates to cloned genes, transformed hosts carrying such cloned genes, and methods of use thereof for producing selected aromatic compounds by the biocatalytic conversion of glucose and other sugars capable of being used in the biosynthesis of such aromatic compounds. Selected genes of the E. coli common aromatic pathway have been cloned and expressed in bacterial hosts. A host carrying vectors for over-expression of the selected genes of the common aromatic pathway plus an additional gene or genes for converting chorismate, the final product of the common aromatic pathway, to a selected aromatic compound results in production of substantial amounts of such selected aromatic compound.

Chorismate is an intermediate in biosynthetic pathways that lead to the production of many aromatic compounds. Because of the large number of aromatic pathways that branch from chorismate, the biosynthetic pathway used by organisms to produce chorismate is often known as the "common aromatic pathway." This pathway is also known as the shikimate pathway because shikimate was the first identified intermediate in the pathway.

Efficient and cost-effective biosynthetic production of chorismate and its biosynthetic derivatives require that carbon sources such as glucose, lactose, galactose, and other sugars be converted to the selected product in high percentage yields. Accordingly, it is valuable from the standpoint of industrial biosynthetic production of aromatic compounds or other biosynthetic derivatives of chorismate to increase the flux of carbon sources into and through the common aromatic pathway, thereby enhancing biosynthesis of chorismate and its derivatives.

The present invention provides for enhanced commitment of cellular carbon sources to enter and flow through the common aromatic pathway by transferring into host cells genetic elements encoding enzymes that catalyze synthesis of the initial carbon compounds of the common aromatic pathway, genetic elements encoding selected enzymes of the common aromatic pathway, and genetic elements encoding enzymes that catalyze conversion of chorismate to a selected aromatic compound. The genetic elements can be in the form of extrachromosomal plasmids, cosmids, phages, or other replicable elements configured for carrying these genetic elements for expression in a host cell.

U.S. Pat. No. 5,168,056 to Frost discloses cloning and expression of transketolase and optionally the aroF gene and/or aroB gene for enhancing diversion of carbon resources into the common aromatic pathway. U.S. Pat. No. 5,272,073 to Frost & Draths describes a method for synthesizing catechol from a carbon source, such as glucose, by creating a pathway that diverges from the common aromatic pathway for conversion of dehydroshikimate to protocatechuate and then to catechol. This divergent pathway is induced by transforming a host with recombinant DNA carrying the transketolase, DAHP synthase, and 3-dehydroquinate synthase genes. U.S. Pat. No. 5,008,190 and U.S. Pat. No. 5,030,567 to Lee et al. describe cloning of the aroF gene and the pheA gene for increasing the biosynthesis of phenylalanine. EP 77196 discloses cloning of a gene that specifies biosynthesis of a DAHP synthase that is resistant to feedback inhibition by aromatic amino acids. R. Meuller et al., 43 Appl. Microbiol. Biotech. 985–88 (1995); M. Seibert et al., 140 Microbiol. 897–904 (1994); G. Wu et al., 139 J. Gen. Microbiol. 17995-1805 (1993); B. P. Nichols et al., 174 J. Bacteriol. 5309–16 (1992); M. Siebert et al., 307 FEBS Lett. 347–50 (1992); L. Heide et al., 175 J. Bacteriol. 5728–29 (1993); H. Matsude et al., JP 96107789, disclose cloning of the chorismate pyruvate lyase gene that encodes the enzyme for converting chorismate to 4-hydroxybenzoic acid. U.S. Pat. No. 5,487,987 to J. Frost et al. discloses synthesis of adipic acid from biomass-derived carbon sources by expression of 3-dehydroshikimate dehydratase and other enzymes for conversion of 3-dehydroshikimate to adipic acid. WO 94/08015 by Frost et al. teaches the synthesis of quinic acid from glucose by cloning and expressing enzymes in the early stages of the common aromatic pathway for synthesis of dehydroquinate and subsequent conversion to quinic acid. WO 95/33843 by Frost et al. describes enhanced efficiency of production of aromatic compounds by cloning and expressing 3-dehydroquinate synthase, shikimate kinase, 5-enolpyruvoyl-shikimate-3-phosphate synthase, and chorismate synthase and optionally with transketolase and DAHP synthase. All of these processes are inadequate for the production of commercially acceptable levels of selected aromatic compounds for which chorismate is a precursor.

In view of the foregoing, it will be appreciated that cloned genes of the common aromatic pathway and additional genes for converting chorismate to a selected aromatic compound, transformed hosts carrying such cloned genes, and methods of using such cloned genes and transformed hosts for producing the selected aromatic compound would be a significant advancement in the art.

BRIEF SUMMARY OF THE INVENTION

It is an object of the present invention to molecularly clone selected genes of the E. coli common aromatic pathway and additional genes for converting chorismate, the final product of the common aromatic pathway, to a selected aromatic compound.

It is another object of the invention to provide transformed hosts carrying the selected cloned genes for over-expression of the selected enzymes of the common aromatic pathway and such additional enzymes necessary for converting chorismate to a selected aromatic compound.

It is also an object of the invention to provide methods for synthesizing a selected aromatic compound by cloning and expressing selected genes of the common aromatic pathway and such additional genes necessary for converting chorismate to the selected aromatic compound.

These and other objects can be achieved by providing a method for producing a compound for which chorismate is an anabolic precursor comprising the steps of:

(a) transforming a microorganism with at least one recombinant plasmid, the at least one recombinant plasmid comprising at least one plasmid vector into which DNA segments that code for DAHP synthase, transketolase, PEP synthase, chorismate synthase, shikimate kinase, EPSP synthase, DHQ synthase, and one or more enzymes for converting chorismate into the compound have been inserted;

(b) culturing the transformed microorganism under conditions that promote the synthesis of the compound.

In preferred embodiment of the invention, the compound is p-hydroxybenzoic acid and the one or more enzymes for converting chorismate comprises chorismate pyruvate lyase.

DETAILED DESCRIPTION OF THE INVENTION

Figure 1:
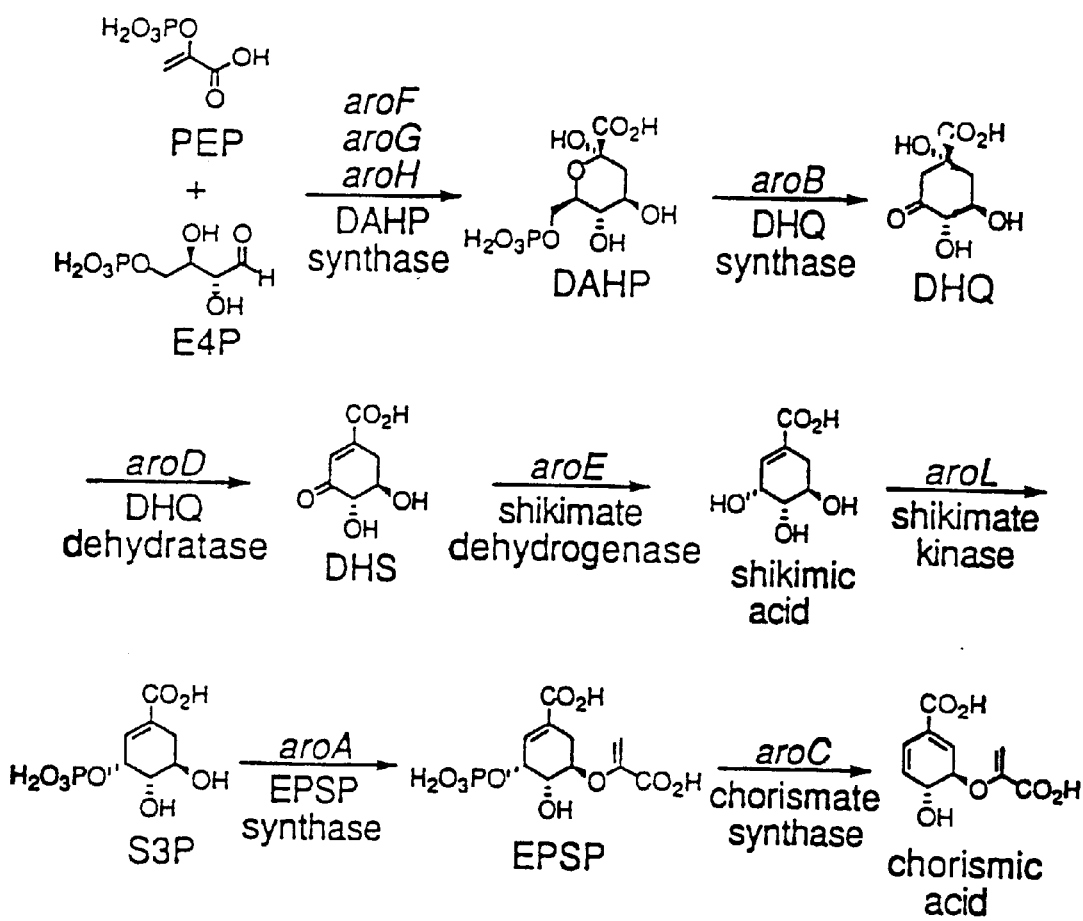
FIG. 1 shows the common aromatic pathway for synthesis of chorismate, a precursor of many aromatic compounds.

Before the present compositions and methods for producing selected aromatic compounds through expression of selected genes in the common aromatic pathway are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "genetic elements" include nucleic acids (DNA or RNA) having expressible coding sequences for products such as proteins, apoproteins, or antisense RNA, which can perform or control common aromatic pathway or related enzymatic functions. The expressed proteins can function as enzymes, repress or derepress enzyme activity, or control expression of enzymes. In addition, genetic elements are defined to include optional expression control elements including promoters, repressors, and enhancers that act to control expression or derepression of coding sequences for proteins, apoproteins, or antisense RNA. For example, such control sequences can be inserted into wild type host cells to promote over-expression of selected enzymes already encoded in the host cell genome, or alternatively can be used to control synthesis of extrachromosomally encoded enzymes.

Aromatic amino acids, and a number of other aromatic compounds are, or can be, derived from the important intermediate chorismate, the final branch-point intermediate of the "common" aromatic pathway, which is shown in FIG. 1. The first committed step of the common aromatic pathway is the condensation of erythrose-4-phosphate (E4P) and phosphoenolpyruvate (PEP). E4P can be produced by a transketolase-catalyzed conversion of carbon sources directed through the transketolase-catalyzed portions of the pentose phosphate pathway, whereas PEP can be produced by PEP synthase. Both E4P and PEP, however, can also be produced by other biosynthetic mechanisms. Isozymes of transketolase (EC 2.2.1.1) are the products of the tktA gene located at 63 min on the E. coli linkage map, as well as the tktB gene. PEP synthase (EC 2.7.9.2) is the product of the ppsA gene located at 37 min on the E. coli linkage map. The condensation of E4P and PEP is an aldol condensation between an intermediate carbanion of C-3 of PEP and the carbonyl C-1 of E4P. The majority of the PEP molecules react stereospecifically with respect to the configuration on C-3, excluding the formation of a freely rotating intermediate methyl group.

The condensation of PEP and E4P is catalyzed by the enzyme DAHP synthase (3-deoxy-D-arabino-heptulosonate-7-phosphate synthase; EC 4.1.2.15). Wild type E. coli produces three DAHP synthase isoenzymes: DAHP synthase (phe), DAHP synthase (tyr), and DAHP synthase (trp), which are sensitive to feedback inhibition by phenylalanine, tyrosine, and tryptophan, respectively. The tetrameric DAHP synthase (phe) has a subunit molecular weight of 35,000, and the dimeric DAHP synthase (tyr) and DAHP synthase (trp) have subunit molecular weights of approximately 40,000. The native forms of the enzymes are probably protein-PEP adducts. In E. coli, the structural genes for DAHP synthase (tyr), DAHP synthase (phe), and DAHP synthase (trp) are aroF, aroG, and aroH, respectively, with gene locations at 56, 17, and 37 min on the E. coli linkage map. In wild type E. coli, 80% of the total DAHP synthase activity is contributed by the phenylalanine-sensitive isoenzyme, and 20% is contributed by the tyrosine-sensitive isoenzyme. There are only traces of the DAHP synthase (trp) in E. coli.

After the committed step, the next reaction of the common aromatic pathway is an intramolecular exchange of the DAHP ring oxygen with C-7, accompanied by an oxidation at C-6 and a reduction at C-2. Cleavage of the phosphoester provides the driving force to form 3-dehydroquinate (DHQ). This reaction is catalyzed by dehydroquinate synthase (DHQ synthase; EC 4.6.1.3), which is the product of the aroB gene located at 75 min on the E coli linkage map. Pure DHQ synthase from E. coli is a single polypeptide chain having a molecular weight of 40,000–44,000. The enzyme requires Co and NAD for activity, the latter in catalytic amounts. The formation of DHQ from DAHP is stereospecific and occurs with inversion of the conformation on C-7 of DAHP without exchange of hydrogen with the reaction medium.

A stereospecific syn-dehydration of DHQ introduces the first double bond of the aromatic ring system to yield 3-dehydroshikimate (DHS). The reaction is catalyzed by 3-dehydroquinate dehydratase (EC 4.2.1.10), the product of the aroD gene located at 37 min on the E. coli linkage map. Schiff base formation between enzyme and substrate causes a conformational change in the substrate (twisted boat) that leads to the stereospecific course of the reaction.

Shikimate biosynthesis from DHS is catalyzed by shikimate dehydrogenase (EC 1.1.1.25), the product of the aroE gene located at 72 min on the E. coli linkage map. This NADP-specific enzyme facilitates the hydrogen transfer from the A-side of NADPH.

Shikimate is phosphorylated to shikimate 3-phosphate (S3P) by shikimate kinase (EC 2.7.1.71). There are two isoenzymes of shikimate kinase in E. coli, shikimate kinase I and shikimate kinase II, which are the products of the aroK and aroL genes, respectively. AroL is located at 9 min on the E. coli linkage map. Since shikimate kinase II is inhibited by chorismate, prephenate, ADP, and 5-enolpyruvoylshikimate 3-phosphate (EPSP) and derepressed by growth on limiting tyrosine, the enzyme is believed to represent a key allosteric control point of the pathway in some types of host cells.

S3P reacts with PEP to form EPSP and inorganic phosphate. This reversible enzyme-catalyzed reaction is a transfer of an unchanged enolpyruvoyl moiety of PEP. Protonation of C-3 of PEP, combined with a nucleophilic attack of the 5-hydroxyl of shikimate, leads to a presumed intermediate from which EPSP is obtained in a 1,2-elimination of orthophosphate. The reaction is catalyzed by EPSP synthase (EC 2.5.1.19), which is the product of the aroA gene located at 20 min on the E. coli linkage map.

The second double bond in the aromatic ring system is introduced through a trans-1,4-elimination of orthophosphate from EPSP to yield chorismate. The reaction is catalyzed by chorismate synthase (EC 4.6.1.4), which is the product of the aroC gene located at 51 min on the E. coli linkage map.

From the key intermediate chorismate, which is the endpoint of the common aromatic pathway, biosynthesis of a diverse number of aromatic compounds is possible. For example, the aromatic amino acids tryptophan, tyrosine, and phenylalanine (which can be a precursor to ASPARTAME) can be synthesized from chorismate along their respective biosynthetic pathways. Other commercially important aromatic compounds also produced from chorismate include folates, melanin, and prephenic acid. Other aromatic compounds or precursors thereof produced from the common aromatic pathway include enterochelin, indigo, indole acetic acid (IAA), p-hydroxybenzoic acid, 3,4-dihydroxybenzoic acid (protocatechuic acid), p-aminobenzoic acid (PABA), folic acid, o-aminobenzoic acid (anthranilic acid), catechol, adipic acid, benzoquinone, hydroquinone, and phenol.

Enhanced expression of genes coding for proteins able to perform or control common aromatic pathway or related enzymatic functions is mediated by genetic elements transferable into a host cell. The nucleic acids encoding these expressible sequences can be either chromosomal (e.g. integrated into a host cell chromosome by homologous recombination or other mechanism) or extrachromosomal (e.g. carried by plasmids, cosmids, and the like).

The genetic elements of the present invention can be introduced into a host cell by plasmids, cosmids, phages, yeast artificial chromosomes, or other vectors that mediate transfer of genetic elements into a host cell. These vectors can include an origin of replication, along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics, such as tetracycline, ampicillin, chloramphenicol, kanamycin, or neomycin.

A preferred means for introducing genetic elements into a host cell uses an extrachromosomal multi-copy plasmid vector into which genetic elements in accordance with the present invention have been inserted. Plasmid-borne introduction of the genetic elements into host cells involves an initial cleaving of a plasmid with a restriction enzyme, followed by ligation of the plasmid and genetic elements in accordance with the invention. Upon recircularization of the ligated recombinant plasmid, transfer into the host cell is carried out, by methods well known in the art such as electroporation, calcium-dependent transformation, and the like. Plasmids suitable for insertion of genetic elements into the host cell include, but are not limited to, pBR322 and its derivatives, such as pAT153, pXf3, pBR325, and pBR327, pUC vectors, pACYC and its derivatives, pSC101 and its derivatives, and ColE1. In addition, cosmid vectors such as pLAFR3 are also suitable for the insertion of the genetic elements into host cells.

Suitable host cells for use in the present invention are members of those genera capable of being utilized for industrial biosynthetic production of desired aromatic compounds. Accordingly, host cells can include prokaryotes belonging to the genera Escherichia, Corynebacterium, Brevibacterium, Arthrobacter, Bacillus, Pseudomonas, Streptomyces, Staphylococcus, Acinetobacter, Klebsiella, or Serratia. Eukaryotic host cells can also be utilized, with yeasts of the genus Saccharomyces or Schizosaccharomyces being preferred.

More specifically, prokaryotic host cells are derived from species that include *Escherichia coli, Klebsiella pneumoniae, Acinetobacter calcoaceticus, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor, Streptomyces griseus, Streptomyces kasugensis, Streptomyces lavenulae, Streptomyces lipmanii, Streptomyces lividans, Staphylococcus epidermis, Staphylococcus saprophyticus,* or *Serratia marcescens*. Preferred eukaryotic host cells include *Saccharomyces cerevisiae* or *Saccharomyces carlsbergensis*.

For industrial production of primary metabolites derived from chorismate (such as aromatic amino acids), deregulated mutant strains of the above recited species that lack feedback inhibition of one or more enzymes in the metabolic biosynthetic pathway are preferred. Such strains can be created by random or directed mutagenesis, or are commercially available. Examples of E. coli strains having DAHP synthase, prephenate dehydratase, or chorismate mutase feedback inhibition removed are described in U.S. Pat. No. 4,681,852 to Tribe and U.S. Pat. No. 4,753,883 to Backman et al.

In preferred embodiments, the present invention is a method for increasing carbon flow into the common aromatic pathway of a host cell and thence to the selected aromatic compound. Increasing carbon flow requires the step of transforming the host cell with recombinant DNA containing selected genes such that the respective gene products are expressed at enhanced levels relative to wild type cells.

Carbon sources useable in accordance with this invention include any carbon sources capable of being biocatalytically converted into E4P and PEP, the immediate precursor compounds to the common aromatic pathway (FIG. 1). Preferred carbon sources to be supplied in the growth medium include glucose, glycerol, xylose, maltose, lactose, lactate, pentoses, fructose, and acetic acid. Other feedstocks that can be used include corn steep liquor, molasses, crude glucose, agricultural or forestry waste products, bagasse, starch, cellulose, and the like. The conditions for growth of the host cells will vary somewhat depending on the genus and species of host cell, but the effects of such factors as temperature, pH, salt concentration, aeration, and the like are already well known in the art or can be determined by a person skilled in the art without undue experimentation. D-glucose is an especially preferred carbon source for use by host cells in accordance with the present invention.

There are many methods for controlling the expression of genes introduced into the host cells. For example, a gratuitous inducer, such as IPTG, is used in the lac repressor-operator system to control the lac operon, A. Itakma et al., 198 Science 1056 (1977); A. Miyanohava et al., 80 Proc. Nat'l Acad. Sci. USA 1 (1983), hereby incorporated by reference. Also, there is a temperature shift method that uses the cI857 repressor of phage lambda. At temperatures below 37° C., the repressor is active and binds to the operator such that transcription does not occur. Al temperatures above 37° C., the repressor becomes inactive and no longer binds to the operator such that the gene or genes under the control of the repressor is expressed. Many other promoter systems are well known in the art and could be used advantageously in the present invention, such as metal inducible promoters, acid/base inducible promoters, and the like.

In developing an industrial process for producing a specific chemical that is synthesized in normal bacterial cells from chorismate, it was decided to clone and over-express the enzymes necessary for its synthesis. Most of the enzymes in the common aromatic pathway of *E. coli* can become bottlenecks, and thus should be over-expressed, but the aroD and aroE gene products, 3-dehydroquinate dehydratase and shikimate dehydrogenase, respectively, are not thought to constitute bottlenecks. That is, the wild type levels of these enzymes in *E. coli* are high enough to prevent any significant buildup of their substrates even when all other enzymes in this pathway are over-expressed. Thus, it was determined to clone the phenylalanine-sensitive DAHP synthase (aroG), aroA, aroB, aroC and shikimate kinase II (aroL) genes of the common aromatic pathway and also the genes coding for transketolase (tktA) and PEP synthase, two enzymes that increase the concentrations of the two substrates, E4P and PEP, that are condensed at the start of the common aromatic pathway. A second reason for cloning PEP synthase is that the reactions producing some of the desired chemicals from chorismate result in release of a molecule of pyruvate, and this pyruvate must be recycled if the process is to be made efficient. Finally, in one illustrative embodiment of the invention, it was determined to clone the ubiC gene, which codes for chorismate pyruvate lyase, the enzyme that produces a selected product, p-hydroxybenzoate (pHB), from chorismate. PHB is commercially important as a precursor for synthesis of certain polymers.

For three of these enzymes, more than one gene in *E. coli* codes for an enzyme possessing the selected activity, and a choice had to be made concerning which gene to clone. In the case of DAHP synthase, there are three isozymes that are sensitive to feedback inhibition by tyrosine, tryptophan, and phenylalanine, respectively. It was determined to clone the phenylalanine-sensitive enzyme for the following reasons. DAHP synthase (phe) has the highest specific activity of the three isozymes, and may be more stable than the tyrosine-sensitive enzyme as the cells enter stationary phase. In addition, it was determined to clone this gene from a bacterial strain (ATCC 31884) containing a mutation that renders the enzyme insensitive to feedback inhibition (feedback resistant), so that its activity would not be reduced even if high levels of phenylalanine built up in the cell. There are also two genes coding for shikimate kinases in *E. coli,* aroK and aroL. It was determined to clone the aroL gene since its product binds shikimate approximately 100 fold more tightly than the enzyme encoded by aroK, and the aroL gene product is thought to be the main shikimate kinase involved in synthesis of aromatic amino acids. There are also two genes encoding transketolase, tktA and tktB. It was determined to clone the tktA gene because the transketolase product of the tktB gene is relatively inefficient.

The genes were cloned using PCR amplification such that only selected portions of the flanking sequences were obtained. Thus, the cloning methodology was not dependent on the fortuitous positions of restriction endonuclease sites to perform the cloning. The regions in which PCR primers were chosen were dictated by the typical structure of genes in *E. coli.* At the 5' end of the gene, primers were designed to amplify the entire protein coding region including the initiation codon (usually AUG) and the Shine-Dalgarno sequence (ribosome binding site) preceding it. If the gene's endogenous promoter was relatively close to the start point of translation and could be included in the amplified product without including any repressor binding sites (operators), which would result in transcriptional control of the cloned gene, the endogenous promoter was also included in the amplified product. This was done because a goal was maximum expression of the cloned genes. If the endogenous promoter was not close to the start point of translation, or could not be included in the amplified product without also including a repressor binding site, the endogenous promoter was not included in the amplified product. This was done because these genes were going to be cloned into an expression vector containing a strong promoter, which would ensure high level expression of the cloned genes whether or not the cloned genes contained endogenous promoters, and because it was determined to be important to avoid any operators exerting negative control over the synthesis of the cloned genes in the final construct. This resulted in a collection of cloned genes, some of which were preceded by their endogenous promoters and some of which were not. At the 3' ends of the genes, the codons responsible for termination of protein synthesis were always included in the amplified segment, but any transcription termination signals were excluded, so that in the final construct, containing several cloned genes in tandem, RNA would be synthesized from all the cloned genes by RNA polymerase.

All these genes from *E. coli* have been sequenced, and a computerized search for primer locations made use of those known sequences. After the appropriate primer sequences were selected from within the appropriate regions by a computer program (Lasergene by DNASTAR), the structures of the primers were modified by addition of the recognition sequences for specific restriction endonucleases at the 5' end of each primer, and then extension of the primers an additional three bases by addition of a so called "clamp" having the sequence "CTC". The specific restriction endonuclease digestion sites added were chosen according to the following criteria. First, the sites were not present in the sequence to be amplified. Second, different restriction sites were designed into the two primers necessary for amplifying a selected gene such that the amplified and digested fragment could be inserted into a doubly digested vector in only one (correct) orientation. Since the vector would also be digested with two different restriction enzymes, there would be much less problem with reclosing of the vector, which results in plasmids lacking inserts. Finally, the restriction sites were chosen from those present in the pUC19 polylinker, C. Yanisch-Perron et al., 33 Gene 103–19 (1985), hereby incorporated by reference, since that polylinker is also present in a wide variety of other vectors. The order in which the genes were to be arranged was predetermined, as will be described in more detail momentarily. Additional considerations included generally choosing restriction sites that are not adjacent to each other in the pUC19 polylinker, due to the difficulty in completely digesting adjacent sites, and choosing sites for which the commercial enzymes are inexpensive and reliable.

The order of the genes in the final construct was dictated by a desired relative level of expression, i.e. placing the gene with the highest desired level of expression closest to the promoter in the vector, the gene with the next highest desired level of expression next closest to the promoter, and so forth. The eight cloned genes were inserted into two plasmids for simplicity and manageability and to make it possible to transfer the synthetic capability to other bacterial strains that are hardier than *E. coli* and may thus be better suited to bioprocessing applications. Thus, one plasmid contained chorismate pyruvate lyase, DAHP synthase, transketolase, and PEP synthase, arranged in that order, based on the desired relative level of expression. The order of the genes in the other plasmid, chorismate synthase, shikimate kinase, EPSP synthase, and DHQ synthase, was selected on the basis of the reverse order of their wild type specific activities. This was done in an attempt to equalize the activity levels in the production strain. AroC has the lowest specific activity in wild type cells, and was placed first, followed by aroL which has the next highest specific activity, and so forth. This order is also relatively consistent with the concept that the last enzyme in a pathway should be expressed at the highest level, the next to last enzyme should be expressed at the next highest level, and so forth, to "pull" metabolic flow through the pathway.

The primers were synthesized on a Cruachem PS250 Automated DNA Synthesizer and then used to amplify the appropriate segments using standard PCR protocols. E.g., U.S. Pat. No. 4,683,195; U.S. Pat. No. 4,683,202; U.S. Pat. No. 4,800,159; U.S. Pat. No. 4,965,188; PCR Technology: Principles and Applications for DNA Amplification (H. Erlich ed., Stockton Press, New York, 1989); PCR Protocols: A guide to Methods and Applications (Innis et al. eds, Academic Press, San Diego, Calif., 1990); hereby incorporated by reference. The annealing temperatures for the PCR reactions were calculated by the computer program. All segments were amplified from the DNA of wild type *E. coli* K-12 (ATCC 25404) except for the DAHP synthase gene, which was amplified from the DNA of a mutant which contained a feedback resistant DAHP synthase (ATCC 31884). Gels were run on the PCR products, and bands of the predicted sizes were obtained in each case. The PCR products were then digested with the two restriction enzymes whose recognition sites had been designed into the two primers and ligated to pUC19 DNA which had been digested with the same two enzymes. The ligation mixtures were introduced into *E. coli* JM109 cells, and the transformants were spread on plates containing ampicillin, 5-bromo-4-chloro-3-indolyl-β-D-galactoside (X-gal), and isopropyl-β-D-thiogalactopyranoside (IPTG). Colonies containing plasmids with inserts are white under these conditions, while colonies containing the vector alone (lacking an insert) are blue, as is well known in the art, J. Sambrook et al., Molecular Cloning (2d ed., 1989), hereby incorporated by reference. Plasmid minipreps were prepared from a number of white colonies and analyzed by gel electrophoresis. In most cases, several independent isolates were identified which contained plasmids of the same size, and that size was approximately what was expected based on the size of the insert to be cloned. These candidates were then digested with the two enzymes used in their construction and again analyzed by electrophoresis, looking for an insert the same size as the PCR fragment used in their construction. Clones containing inserts of the proper size were further analyzed using a variety of restriction enzymes to determine whether their structures matched the restriction map generated from the known sequence, and in all cases they did. The lone gene that could not be cloned in this manner was aroC. This gene was cloned by complementation of an aroC mutant strain, AB2849 (CGSC#2849, *E. coli* Genetic Stock Center, Yale University, New Haven, Conn.). Such a strain will not grow on minimal medium, as it cannot synthesize aromatic amino acids. The mutant was transformed with a ligation mixture as described above and plated on minimal medium. Plasmids were prepared from colonies growing on minimal medium and analyzed as above, resulting in cloning of the aroC gene. This cloned gene was further tested by retransforming the aroC mutant cells and demonstrating that a large number of cells capable of growing on minimal medium were produced. Thus the plasmid does possess aroC complementing activity.

Finally, to construct the plasmids containing multiple genes, the various cloned genes were excised from their individual plasmids with the appropriate restriction enzymes, in most cases the restriction enzymes used to originally clone them, and then mixed together in equimolar ratios with the vector digested with the appropriate two restriction enzymes, usually for the first and last restriction enzyme sites in the polylinker, and the ligation and transformation were performed as above. Minipreps from several white colonies were screened by electrophoresis, and those having the appropriate size, as predicted from the sum of the sizes of the insert fragments, were further analyzed by restriction enzyme digestion. Each gene was individually cut out of the multi-gene plasmid, and the fragment obtained was compared to that obtained by digestion of the plasmid containing the particular cloned gene alone. Further digests (overlapping) were performed and compared with the restriction map predicted by combining the maps of the individual genes. These manipulations resulted in introduction of the ubiC, DAHP synthase, transketolase, and PEP synthase genes into pUC19, a plasmid possessing a ColE1 origin of replication and an ampicillin resistance gene. The other four genes (aroC, L, A, and B) were introduced into the vector pSU19, Bartolome et al., 102 Gene 75–78 (1991), hereby incorporated by reference, which contains a p15A origin of replication (compatible with the ColE1 origin of pUC19) and a chloramphenicol resistance gene. Finally these two plasmids were introduced together into cells of a number of *E. coli* strains, and those strains were analyzed for the amount of the desired product they were able to produce, which is a substantial amount.

Gel electrophoresis, restriction endonuclease digestion, ligation, transformation, plasmid preparation, and restriction mapping were all carried out according to methods well known in the art. E.g., J. Sambrook et al., Molecular Cloning: A Laboratory Manual (2d ed., 1989); T. Maniatis et al., Molecular Cloning: A Laboratory Manual (1982); F. Ausubel et al., Current Protocols in Molecular Biology (1987), hereby incorporated by reference.

EXAMPLE 1

The *E. coli* ubiC gene encoding chorismate pyruvate lyase was cloned after amplifying the gene using oligonucleotide primers according to methods well known in the art. Primers for amplification and cloning of the ubiC gene were SEQ ID NO:1 and SEQ ID NO:2. The template DNA was *E. coli* K-12 ATCC 25404 chromosomal DNA. The amplified DNA fragment was digested with HindIII and PstI, and the resulting double-digested amplified DNA was then ligated into pUC19 that had also been double digested with the same two restriction endonucleases. The ligated DNA was transformed into competent JM109 cells, plated on indicator plates containing ampicillin, IPTG, and X-gal, and white colonies were selected for analysis. Plasmid minipreps were prepared, and the plasmid DNA was digested with HindIII and PstI and fractionated by gel electrophoresis. The resulting DNA bands were of the expected size based on comparison to DNA standards and the PCR-amplified product. The sequence of the resulting cloned ubiC gene is described herein as SEQ ID NO:24.

EXAMPLE 2

In this example, the aroG gene encoding DAHP synthase (phe) was cloned into pUC19 according to the procedure of Example 1, except that the primers used for amplification of the gene were SEQ ID NO:3 and SEQ ID NO:4, the template DNA was E. coli ATCC 31884, and the amplified DNA and vector DNA were digested with SalI and BamHI. The sequence of the cloned DAHP synthase (phe) gene is described herein as SEQ ID NO:17.

EXAMPLE 3

In this example, the tktA gene encoding transketolase was cloned into pUC19 according to the procedure of Example 1, except that the primers used for amplification of the gene were SEQ ID NO:5 and SEQ ID NO:6, and the amplified DNA and vector DNA were digested with BamHI and SacI. The sequence of the cloned transketolase gene is described herein as SEQ ID NO:18.

EXAMPLE 4

In this example, the ppsA gene encoding PEP synthase was cloned into pUC19 according to the procedure of Example 1, except that the primers used for amplification of the gene were SEQ ID NO:7 and SEQ ID NO:8, and the amplified DNA and vector DNA were digested with SacI and EcoRI. The sequence of the cloned PEP synthase gene is described herein as SEQ ID NO:19.

EXAMPLE 5

In this example, the cloned ubiC, aroG, tktA, and ppsA genes of Examples 1–4 were recloned in pUC19 as follows. The ubiC gene in pUC19 was removed from the plasmid cloning vector by digestion with HindIII and PstI, and the DNA fragment containing the ubiC gene was purified by gel electrophoresis. The aroG gene in pUC19 was removed from the plasmid cloning vector by digestion with PstI and BamHI, and the DNA fragment containing the aroG gene was purified by electrophoresis. The tktA gene in pUC19 was removed from the plasmid cloning vector by digestion with BamHI and SacI, and the DNA fragment containing the tktA gene was purified by gel electrophoresis. The ppsA gene in pUC19 was removed from the plasmid cloning vector by digestion with SacI and EcoRI, and the DNA fragment containing the ppsA gene was purified by gel electrophoresis. Equimolar amounts of these four purified genes and of pUC19 digested with HindIII and EcoRI were then ligated together in a batch, transformed into competent JM109 cells, and plated on indicator plates. White colonies were selected, plasmid minipreps prepared, and the plasmid DNA analyzed by restriction mapping. A plasmid comprising all four of the genes in the correct order in pUC19 was designated pME2. The sequence of the cloned genes is described herein as SEQ ID NO:25.

EXAMPLE 6

In this example, the aroC gene encoding chorismate synthase was cloned into pSU19 according to the procedure of Example 1, except that the primers used for amplification of the gene were SEQ ID NO:9 and SEQ ID NO:10, the amplified DNA and pSU19 vector DNA were digested with HindIII and PstI, and recombinant plasmids were selected by complementation by transformation into an aroC-deficient strain, AB2849 (CGSC#2849) and growth on minimal medium. The sequence of the cloned aroC gene is described herein as SEQ ID NO:20.

EXAMPLE 7

In this example, the aroL gene encoding shikimate kinase II was cloned into pSU19 according to the procedure of Example 1 except that the primers used for amplification of the gene were SEQ ID NO:11 and SEQ ID NO:12, the amplified DNA and pSU19 vector DNA were digested with PstI and XbaI, and the indicator plates contained chloramphenicol instead of ampicillin. The sequence of the cloned aroL gene is described herein as SEQ ID NO:21.

EXAMPLE 8

In this example, the aroA gene encoding EPSP synthase was cloned into pSU19 according to the procedure of Example 1, except that the primers used for amplification of the gene were SEQ ID NO:13 and SEQ ID NO:14, the amplified DNA and pSU19 vector DNA were digested with XbaI and KpnI, and the indicator plates contained chloramphenicol instead of ampicillin. The sequence of the cloned aroA gene is described herein as SEQ ID NO:22.

EXAMPLE 9

In this example, the aroB gene encoding 3-dehydroquinate synthase was cloned into pSU19 according to the procedure of Example 1, except that the primers used for amplification of the gene were SEQ ID NO:15 and SEQ ID NO:16, the amplified DNA and pSU19 vector DNA were digested with KpnI and EcoRI, and the indicator plates contained chloramphenicol instead of ampicillin. The sequence of the cloned aroB gene is disclosed herein as SEQ ID NO:23.

EXAMPLE 10

In this example, the cloned aroC, aroL, aroA, and aroB genes of Examples 6–9 were recloned in pSU19 as follows. The aroC gene in pSU19 was removed from the cloning vector by digestion with HindIII and PstI, and the DNA fragment containing the aroC gene was purified by gel electrophoresis. The aroL gene in pSU19 was removed from the cloning vector by digestion with PstI and XbaI, and the DNA fragment containing the aroL gene was purified by electrophoresis. The aroA gene in pSU19 was removed from the cloning vector by digestion with XbaI and KpnI, and the DNA fragment containing the aroA gene was purified by gel electrophoresis. The aroB gene in pSU19 was removed from the cloning vector by digestion with KpnI and EcoRI, and the DNA fragment containing the aroB gene was purified by gel electrophoresis. Equimolar amounts of these four purified genes and of pSU19 digested with HindIII and EcoRI were then ligated together in a batch, transformed into competent E. coli JM109 cells, and plated on indicator plates containing chloramphenicol. White colonies were selected, plasmid minipreps prepared, and the plasmid DNA analyzed by gel electrophoresis and restriction mapping. A plasmid comprising all four of the genes in the correct order in pSU19 was designated pME4. The sequence of the cloned genes is disclosed herein as SEQ ID NO:26.

EXAMPLE 11

In this example, competent *E. coli* ATCC 25404 cells were transformed with both pME2 and pME4, and colonies were selected on plates containing both ampicillin and chloramphenicol. Plasmid minipreps were prepared, and plasmid DNA was analyzed by gel electrophoresis. A colony containing both pME2 and pME4 was grown at 37° C. in broth containing ampicillin, chloramphenicol, and 1 mM IPTG. After 48–72 hours, a substantial increase in pHB was detected as compared to *E. coli* 25404 cells not bearing pME2 and pME4.

We claim:

1. A method of producing p-hydroxybenzoic acid comprising:
   (a) transforming a microorganism with at least one recombinant plasmid, said at least one recombinant plasmid comprising at least one vector into which DNA segments that code for chorismate pyruvate lyase, DAHP synthase, transketolase, and PEP synthase have been inserted and are transcribed from a first promoter and DNA segments that code for chorismate synthase, shikimate kinase, EPSP synthase, and DHQ synthase have been inserted and are transcribed from a second promoter;
   (b) culturing the transformed microorganism under conditions that promote the synthesis of p-hydroxybenzoic acid.

2. A method for producing p-hydroxybenzoic acid biocatalytically in a microbial cell transformant via the common pathway of aromatic compounds synthesis, said method comprising:
   culturing the cell transformant in media containing an assimilable carbon source under conditions conducive to the assimilation of said carbon source, said cell transformant comprising exogenous DNA sequences encoding DAHP synthase, transketolase, PEP synthase, chorismate synthase, shikimate kinase, EPSP synthase, DHQ synthase, and chorismate pyruvate lyase, wherein said exogenous DNA sequences encoding chorismate pyruvate lyase, DAHP synthase, transketolase, and PEP synthase are transcribed from a first promoter, and said exogenous DNA sequences encoding chorismate synthase, shikimate kinase, EPSP synthase, and DHQ synthase are transcribed from a second promoter.

3. The method of claim 2 wherein said exogenous DNA sequences are borne on at least one vector.

4. The method of claim 3 wherein said exogenous DNA sequences are represented as SEQ ID NO:25 and SEQ ID NO:26.

5. The method of claim 1 wherein the DNA segment that codes for chorismate pyruvate lyase is SEQ ID NO:24.

6. The method of claim 1 wherein the DNA segment that codes for DAHP synthase is SEQ ID NO:17.

7. The method of claim 1 wherein the DNA segment that codes for transketolase is SEQ ID NO:18.

8. The method of claim 1 wherein the DNA segment that codes for PEP synthase is SEQ ID NO:19.

9. The method of claim 1 wherein the DNA segments that code for chorismate pyruvate lyase, DAHP synthase, transketolase, and PEP synthase are SEQ ID NO:25.

10. The method of claim 1 wherein the DNA segment that codes for chorismate synthase is SEQ ID NO:20.

11. The method of claim 1 wherein the DNA segment that codes for shikimate kinase is SEQ ID NO:21.

12. The method of claim 1 wherein the DNA segment that codes for EPSP synthase is SEQ ID NO:22.

13. The method of claim 1 wherein the DNA segment that codes for DHQ synthase is SEQ ID NO:23.

14. The method of claim 1 wherein the DNA segments that code for chorismate synthase, shikimate kinase, EPSP synthase, and DHQ synthase are SEQ ID NO:26.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:1:

CTCAAGCTTC TTTTCAGCTC CAAATCTCA                                     29

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (xi) SEQUENCE DESCRIPTION: SEQ ID NO:2:

CTCCTGCAGC TGCGTCAGAC TCCACTCC                                      28

(2) INFORMATION FOR SEQ ID NO:3:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:3:

CTCGRCGACA CCCCGTTTAC ACATTCTGA                                     29

(2) INFORMATION FOR SEQ ID NO:4:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:4:

CTCGGATCCA TCGGATACGC CACTCTGAC                                     29

(2) INFORMATION FOR SEQ ID NO:5:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (xi) SEQUENCE DESCRIPTION: SEQ ID NO:5:

CTCGGATCCT CCCGGCGTAG CCCAAAAC                                      28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:6:

CTCGAGCTCC CGCAAACGGA CATTATCA                                          28

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:7:

CTCGAGCTCA AATGCGCAGA AATGTGTTT                                        29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:8:

CTCGAATTCC CGGGGATTTA TTTTATTTC                                        29

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:9:

CTCAAGCTTA TAACGGCGGC GATGGTGTG                                        29

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:10:

CTCCTGCAGA GCGCAATCGC GGTTTTATT                                        29

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:11:

CTCCTGCAGT GATGGTATGA TCGCTATTC                                        29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:12:

```
CTCTCTAGAT TCCTTATTTC ACGGGATGA                                    29
```

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:13:

```
CTCTCTAGAC CAGCCTGTGG GGTTTTTAT                                    29
```

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:14:

```
CTCGGTACCT TGCCCGTTGT TCATTCAGG                                    29
```

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:15:

```
CTCGGTACCG TTGGCCAATG AACGAATCC                                    29
```

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:16:

```
CTCGAATTCC TTGATAAGCG GCCTGACCT                                    29
```

(2) INFORMATION FOR SEQ ID NO:17:

(i) SEQUENCE CHARACTERISTICS:
        (A) LENGTH: 1188 base pairs
        (B) TYPE: nucleic acid
        (C) STRANDEDNESS: double
        (D) TOPOLOGY: linear (xi) SEQUENCE DESCRIPTION: SEQ ID NO:17:

```
CAGGTCGACA CCCCGTTTAC ACATTCTGAC GGAAGATATA GATTGGAAGT              50
ATTGCATTCA CTAAGATAAG TATGGCAACA CTGGAACAGA CATGAATTAT             100
```

| | |
|---|---|
| CAGAACGACG ATTTACGCAT CAAAGAAATC AAAGAGTTAC TTCCTCCTGT | 150 |
| CGCATTGCTG GAAAAATTCC CCGCTACTGA AAATGCCGCG AATACGGTTG | 200 |
| CCCATGCCCG AAAAGCGATC CATAAGATCC TGAAAGGTAA TGATGATCGC | 250 |
| CTGTTGGTTG TGATTGGCCC ATGCTCAATT CATGATCCTG TCGCGGCAAA | 300 |
| AGAGTATGCC ACTCGCTTGC TGGCGCTGCG TGAAGAGCTG AAAGATGAGC | 350 |
| TGGAAATCGT AATGCGCGTC TATTTTGAAA AGCCGCGTAC CACGGTGGGC | 400 |
| TGGAAAGGGC TGATTAACGA TCCGCATATG GATAATAGCT TCCAGATCAA | 450 |
| CGACGGTCTG CGTATAGCCC GTAAATTGCT GCTTGATATT AACGACAGCG | 500 |
| GTCTGCCAGC GGCAGGTGAG TTTCTCGATA TGATCACCCC ACAATATCTC | 550 |
| GCTGACCTGA TGAGCTGGGG CGCAATTGGC GCACGTACCA CCGAATCGCA | 600 |
| GGTGCACCGC GAACTGGCAT CAGGGCTTTC TTGTCCGGTC GGCTTCAAAA | 650 |
| ATGGCACCGA CGGTACGATT AAAGTGGCTA TCGATGCCAT TAATGCCGCC | 700 |
| GGTGCGCCGC ACTGCTTCCT GTCCGTAACG AAATGGGGGC ATTCGGCGAT | 750 |
| TGTGAATACC AGCGGTAACG GCGATTGCCA TATCATTCTG CGCGGCGGTA | 800 |
| AAGAGCCTAA CTACAGCGCG AAGCACGTTG CTGAAGTGAA AGAAGGGCTG | 850 |
| AACAAAGCAG GCCTGCCAGC ACAGGTGATG ATCGATTTCA GCCATGCTAA | 900 |
| CTCGTCCAAA CAATTCAAAA AGCAGATGGA TGTTTGTGCT GACGTTTGCC | 950 |
| AGCAGATTGC CGGTGGCGAA AAGGCCATTA TTGGCGTGAT GGTGGAAAGC | 1000 |
| CATCTGGTGG AAGGCAATCA GAGCCTCGAG AGCGGGGAGC CGCTGGCCTA | 1050 |
| CGGTAAGAGC ATCACCGATG CCTGCATCGG CTGGGAAGAT ACCGATGCTC | 1100 |
| TGTTACGTCA ACTGGCGAAT GCAGTAAAAG CGCGTCGCGG GTAAGGTTTA | 1150 |
| ATTGTCGGAT GCGCCGTCAG AGTGGCGTAT CCGATGGA | 1188 |

(2) INFORMATION FOR SEQ ID NO:18:

(i) SEQUENCE CHARACTERISTICS:
        (A) LENGTH: 2143 base pairs
        (B) TYPE: nucleic acid
        (C) STRANDEDNESS: double
        (D) TOPOLOGY: linear (xi) SEQUENCE DESCRIPTION: SEQ ID NO:18:

| | |
|---|---|
| TCCTCCCGGC GTAGCCCAAA ACGCGCTGTC GTCAAGTCGT TAAGGGCGTG | 50 |
| CCCTTCATCA TCCGATCTGG AGTCAAAATG TCCTCACGTA AAGAGCTTGC | 100 |
| CAATGCTATT CGTGCGCTGA GCATGGACGC AGTACAGAAA GCCAAATCCG | 150 |
| GTCACCCGGG GGCCCCTATG GGTATGGCTG ACATTGCCGA AGTCCTGTGG | 200 |
| CGTGATTTCC TGAAACACAA CCCGCAGAAT CCGTCCTGGG CTGACCGTGA | 250 |
| CCGCTTCGTG CTGTCCAACG GCCACGGCTC CATGCTGATC TACAGCCTGC | 300 |
| TGCACCTCAC CGGTTACGAT CTGCCGATGG AAGAACTGAA AAACTTCCGT | 350 |
| CAGCTGCACT CTAAAACTCC GGGTCACCCG GAAAGTGGGG TTACACCGCT | 400 |
| GGGTGTGGAA ACCACCACCG GTCCGCTGGG TCAGGGTATT GCCAACGCAG | 450 |
| TCGGTATGGC GATTGCAGAA AAAACGCTGG CGGCGCAGTT TAACCGTCCG | 500 |
| GGCCACGACA TTGTCGACCA CTACACCTAC GCCTTCATGG GCGACGGCTG | 550 |
| CATGATGGAA GGCATCTCCC ACGAAGTTTG CTCTCTGGCG GGTACGCTGA | 600 |

```
AGCTGGGTAA ACTGATTGCA TTCTACGATG ACAACGGTAT TTCTATCGAT        650

GGTCACGTTG AAGGCTGGTT CACCGACGAC ACCGCAATGC GTTTCGAAGC        700

TTACGGCTGG CACGTTATTC GCGACATCGA CGGTCATGAC GCGGCATCTA        750

TCAAACGCGC AGTAGAAGAA GCGCGCGCAG TGACTGACAA ACCTTCCCTG        800

CTGATGTGCA AAACCATCAT CGGTTTCGGT TCCCCGAACA AAGCCGGTAC        850

CCACGACTCC CACGGTGCGC CGCTGGGCGA CGCTGAAATT GCCCTGACCC        900

GCGAACAACT GGGCTGGAAA TATGCGCCGT TCGAAATCCC GTCTGAAATC        950

TATGCTCAGT GGGATGCGAA AGAAGCAGGC CAGGCGAAAG AATCCGCATG       1000

GAACGAGAAA TTCGCTGCTT ACGCGAAAGC TTATCCGCAG GAAGCCGCTG       1050

AATTTACCCG CCGTATGAAA GGCGAAATGC CGTCTGACTT CGACGCTAAA       1100

GCGAAAGAGT TCATCGCTAA ACTGCAGGCT AATCCGGCGA AAATCGCCAG       1150

CCGTAAAGCG TCTCAGAATG CTATCGAAGC GTTCGGTCCG CTGTTGCCGG       1200

AATTCCTCGG CGGTTCTGCT GACCTGGCGC CGTCTAACCT GACCCTGTGG       1250

TCTGGTTCTA AAGCAATCAA CGAAGATGCT GCGGGTAACT ACATCCACTA       1300

CGGTGTTCGC GAGTTCGGTA TGACCGCGAT TGCTAACGGT ATCTCCCTGC       1350

ACGGTGGCTT CCTGCCGTAC ACCTCCACCT TCCTGATGTT CGTGGAATAC       1400

GCACGTAACG CCGTACGTAT GGCTGCGCTG ATGAAACAGC GTCAGGTGAT       1450

GGTTTACACC CACGACTCCA TCGGTCTGGG CGAAGACGGG CCGACTCACC       1500

AGCCGGTTGA GCAGGTCGCT TCTCTGCGCG TAACCCCGAA CATGTCTACA       1550

TGGCGTCCGT GTGACCAGGT TGAATCCGCG GTCGCGTGGA AATACGGTGT       1600

TGAGCGTCAG GACGGCCCGA CCGCACTGAT CCTCTCCCGT CAGAACCTGG       1650

CGCAGCAGGA ACGAACTGAA GAGCAACTGG CAAACATCGC GCGCGGTGGT       1700

TATGTGCTGA AAGACTGCGC CGGTCAGCCG GAACTGATTT TCATCGCTAC       1750

CGGTTCAGAA GTTGAACTGG CTGTTGCTGC CTACGAAAAA CTGACTGCCG       1800

AAGGCGTGAA AGCGCGCGTG GTGTCCATGT CGTCTACCGA CGCATTTGAC       1850

AAGCAGGATG CTGCTTACCG TGAATCCGTA CTGCCGAAAG CGGTTACTGC       1900

ACGCGTTGCT GTAGAAGCGG GTATTGCTGA CTACTGGTAC AAGTATGTTG       1950

GCCTGAACGG TGCTATCGTC GGTATGACCA CCTTCGGTGA ATCTGCTCCG       2000

GCAGAGCTGC TGTTTGAAGA GTTCGGCTTC ACTGTTGATA CGTTGTTGC       2050

GAAAGCAAAA GAACTGCTGT AATTAGCATT TCGGGTAAAA AAGGTCGCTT       2100

CGGCGACCTT TTTTATTACC TTGATAATGT CCGTTTGCGG GAG             2143

(2) INFORMATION FOR SEQ ID NO:19:

(i) SEQUENCE CHARACTERISTICS:
        (A) LENGTH: 2456 base pairs
        (B) TYPE: nucleic acid
        (C) STRANDEDNESS: double
        (D) TOPOLOGY: linear (xi) SEQUENCE DESCRIPTION: SEQ ID NO:19:

CTCAAATGCG CAGAAATGTG TTTCTCAAAC CGTTCATTTA TCACAAAAGG         50

ATTGTTCGAT GTCCAACAAT GGCTCGTCAC CGCTGGTGCT TTGGTATAAC        100

CAACTCGGCA TGAATGATGT AGACAGGGTT GGGGGCAAAA ATGCCTCCCT        150
```

-continued

```
GGGTGAAATG ATTACTAATC TTTCCGGAAT GGGTGTTTCC GTTCCGAATG        200
GTTTCGCCAC AACCGCCGAC GCGTTTAACC AGTTTCTGGA CCAAAGCGGC        250
GTAAACCAGC GCATTTATGA ACTGCTGGAT AAAACGGATA TTGACGATGT        300
TACTCAGCTT GCGAAAGCGG GCGCGCAAAT CCGCCAGTGG ATTATCGACA        350
CTCCCTTCCA GCCTGAGCTG GAAAACGCCA TCCGCGAAGC CTATGCACAG        400
CTTTCCGCCG ATGACGAAAA CGCCTCTTTT GCGGTGCGCT CCTCCGCCAC        450
CGCAGAAGAT ATGCCGGACG CTTCTTTTGC CGGTCAGCAG GAAACCTTCC        500
TCAACGTTCA GGGTTTTGAC GCCGTTCTCG TGGCAGTGAA ACATGTATTT        550
GCTTCTCTGT TTAACGATCG CGCCATCTCT TATCGTGTGC ACCAGGGTTA        600
CGATCACCGT GGTGTGGCGC TCTCCGCCGG TGTTCAACGG ATGGTGCGCT        650
CTGACCTCGC ATCATCTGGC GTGATGTTCT CCATTGATAC CGAATCCGGC        700
TTTGACCAGG TGGTGTTTAT CACTTCCGCA TGGGGCCTTG GTGAGATGGT        750
CGTGCAGGGT GCGGTTAACC CGGATGAGTT TTACGTGCAT AAACCGACAC        800
TGGCGGCGAA TCGCCCGGCT ATCGTGCGCC GCACCATGGG GTCGAAAAAA        850
ATCCGCATGG TTTACGCGCC GACCCAGGAG CACGGCAAGC AGGTTAAAAT        900
CGAAGACGTA CCGCAGGAAC AGCGTGACAT CTTCTCGCTG ACCAACGAAG        950
AAGTGCAGGA ACTGGCAAAA CAGGCCGTAC AAATTGAGAA ACACTACGGT       1000
CGCCCGATGG ATATTGAGTG GGCGAAAGAT GGCCACACCG GTAAACTGTT       1050
CATTGTGCAG GCGCGTCCGG AAACCGTGCG CTCACGCGGT CAGGTCATGG       1100
AGCGTTATAC GCTGCATTCA CAGGGTAAGA TTATCGCCGA AGGCCGTGCT       1150
ATCGGTCATC GCATCGGTGC GGGTCCGGTG AAAGTCATCC ATGACATCAG       1200
CGAAATGAAC CGCATCGAAC CTGGCGACGT GCTGGTTACT GACATGACCG       1250
ACCCGGACTG GGAACCGATC ATGAAGAAAG CATCTGCCAT CGTCACCAAC       1300
CGTGGCGGTC GTACCTGTCA CGCGGCGATC ATCGCTCGTG AACTGGGCAT       1350
TCCGGCGGTA GTGGGCTGTG GAGATGCAAC AGAACGGATG AAAGACGGTG       1400
AGAACGTCAC TGTTTCTTGT GCCGAAGGTG ATACCGGTTA CGTCTATGCG       1450
GAGTTGCTGG AATTTAGCGT GAAAAGCTCC AGCGTAGAAA CGATGCCGGA       1500
TCTGCCGTTG AAAGTGATGA TGAACGTCGG TAACCCGGAC CGTGCTTTCG       1550
ACTTCGCCTG CCTACCGAAC GAAGGCGTGG GCCTTGCGCG TCTGGAATTT       1600
ATCATCAACC GTATGATTGG CGTCCACCCA CGCGCACTGC TTGAGTTTGA       1650
CGATCAGGAA CCGCAGTTGC AAAACGAAAT CCGCGAGATG ATGAAAGGTT       1700
TTGATTCTCC GCGTGAATTT TACGTTGGTC GTCTGACTGA AGGGATCGCG       1750
ACGCTGGGTG CCGCGTTTTA TCCGAAGCGC GTCATTGTCC GTCTCTCTGA       1800
TTTTAAATCG AACGAATATG CCAACCTGGT CGGTGGTGAG CGTTACGAGC       1850
CAGATGAAGA GAACCCGATG CTCGGCTTCC GTGGCGCGGG CCGCTATGTT       1900
TCCGACAGCT TCCGCGACTG TTTCGCGCTG GAGTGTGAAG CAGTGAAACG       1950
TGTGCGCAAC GACATGGGAC TGACCAACGT TGAGATCATG ATCCCGTTCG       2000
TGCGTACCGT AGATCAGGCG AAAGCGGTGG TTGAAGAACT GGCGCGTCAG       2050
GGGCTGAAAC GTGGCGAGAA CGGGCTGAAA ATCATCATGA TGTGTGAAAT       2100
```

```
CCCGTCCAAC GCCTTGCTGG CCGAGCAGTT CCTCGAATAT TTCGACGGCT         2150

TCTCAATTGG CTCAAACGAT ATGACGCAGC TGGCGCTCGG TCTGGACCGT         2200

GACTCCGGCG TGGTGTCTGA ATTGTTCGAT GAGCGCAACG ATGCGGTGAA         2250

AGCACTGCTG TCGATGGCTA TCCGTGCCGC GAAGAAACAG GGCAAATATG         2300

TCGGGATTTG CGGTCAGGGT CCGTCCGACC ACGAAGACTT TGCCGCATGG         2350

TTGATGGAAG AGGGGATCGA TAGCCTGTCT CTGAACCCGG ACACCGTGGT         2400

GCAAACCTGG TTAAGCCTGG CTGAACTGAA GAAATAAAAT AAATCCCCGG         2450

GAATTC                                                         2456
```

(2) INFORMATION FOR SEQ ID NO:20:

(i) SEQUENCE CHARACTERISTICS:
        (A) LENGTH: 1239 base pairs
        (B) TYPE: nucleic acid
        (C) STRANDEDNESS: double
        (D) TOPOLOGY: linear (xi) SEQUENCE DESCRIPTION: SEQ ID NO:20:

```
AAGCTTATAA CGGCGGCGAT GGTGTGTTTA TGCTCACCAA AGAGCAGCTT           50

ATTGCCGCAC GAGAACATTT CGCGATTTAT AAAGATTAAG TAAACACGCA          100

AACACAACAA TAACGGAGCC GTGATGGCTG AAACACAAT TGGACAACTC           150

TTTCGCGTAA CCACCTTCGG CGAATCGCAC GGGCTGGCGC TCGGCTGCAT          200

CGTCGATGGT GTTCCGCCAG GCATTCCGCT GACGGAAGCG GACCTGCAAC          250

ATGACCTCGA CCGTCGTCGC CCTGGGACAT CGCGCTATAC CACCCAGCGC          300

CGCGAGCCGG ATCAGGTCAA AATTCTCTCC GGTGTTTTTG AAGGCGTTAC          350

TACCGGCACC AGCATTGGCT TGTTGATCGA AAACACTGAC CAGCGCTCTC          400

AGGATTACAG TGCGATTAAG GACGTTTTCC GTCCAGGCCA TGCCGATTAC          450

ACCTACGAAC AAAAATACGG TCTGCGCGAT TATCGCGGCG GTGGACGTTC          500

TTCCGCCCGC GAAACCGCCA TGCGCGTGGC GGCAGGAGCT ATTGCCAAAA          550

AATATCTCGC CGAGAAATTT GGTATTGAAA TCCGTGGCTG CCTGACCCAG          600

ATGGGCGACA TTCCGCTGGA TATCAAAGAC TGGTCGCAGG TCGAGCAAAA          650

TCCGTTTTTT TGCCCGGACC CCGACAAAAT CGACGCGTTA GACGAGTTGA          700

TGCGTGCGCT GAAAAAAGAG GGCGACTCCA TCGGCGCTAA AGTCACCGTT          750

GTTGCCAGTG GCGTTCCTGC CGGACTTGGC GAGCCGGTCT TTGACCGCCT          800

GGATGCTGAC ATCGCCCATG CGCTGATGAG CATCAACGCG GTGAAAGGCG          850

TGGAAATTGG CGACGGCTTT GACGTGGTGG CGCTGCGCGG CAGCCAGAAC          900

CGCGATGAAA TCACCAAAGA CGGTTTCCAG AGCAACCATG CGGGCGGCAT          950

TCTCGGCGGT ATCAGCAGCG GGCAGCAAAT CATTGCCCAT ATGGCGCTGA         1000

AACCGACCTC CAGCATTACC GTGCCGGGTC GTACCATTAA CCGCTTTGGC         1050

GAAGAAGTTG AGATGATCAC CAAAGGCCGT CACGATCCCT GTGTCGGGAT         1100

CCGCGCAGTG CCGATCGCAG AAGCGAATGC TGGCGATCGT TTTAATGGAT         1150

CACCTGTTAC GGCAACGGGC GCAAAATGCC GATGTGAAGA CTGATATTCC         1200

ACGCTGGTAA AAAATGAATA AAACCGCGAT TGCGCTCTG                     1239
```

(2) INFORMATION FOR SEQ ID NO:21:

(i) SEQUENCE CHARACTERISTICS:
    (A) LENGTH: 643 base pairs
    (B) TYPE: nucleic acid
    (C) STRANDEDNESS: double
    (D) TOPOLOGY: linear (xi) SEQUENCE DESCRIPTION: SEQ ID NO:21:

| | | |
|---|---|---|
| CAGTGATGGT ATGATCGCTA TTCTCATGAC ACCGGCTTTC GCGCATTGCG | 50 |
| ACCTATTGGG GAAAACCCAC GATGACACAA CCTCTTTTTC TGATCGGGCC | 100 |
| TCGGGGCTGT GGTAAAACAA CGGTCGGAAT GGCCCTTGCC GATTCGCTTA | 150 |
| ACCGTCGGTT TGTCGATACC GATCAGTGGT TGCAATCACA GCTCAATATG | 200 |
| ACGGTCGCGG AGATCGTCGA AAGGGAAGAG TGGGCGGGAT TTCGCGCCAG | 250 |
| AGAAACGGCG GCGCTGGAAG CGGTAACTGC GCCATCCACC GTTATCGCTA | 300 |
| CAGGCGGCGG CATTATTCTG ACGGAATTTA ATCGTCACTT CATGCAAAAT | 350 |
| AACGGGATCG TGGTTTATTT GTGTGCGCCA GTATCAGTCC TGGTTAACCG | 400 |
| ACTGCAAGCT GCACCGGAAG AAGATTTACG GCCAACCTTA ACGGGAAAAC | 450 |
| CGCTGAGCGA AGAAGTTCAG GAAGTGCTGG AAGAACGCGA TGCGCTATAT | 500 |
| CGCGAAGTTG CGCATATTAT CATCGACGCA ACAAACGAAC CCAGCCAGGT | 550 |
| GATTTCTGAA ATTCGCAGCG CCCTGGCACA GACGATCAAT TGTTGATTTT | 600 |
| CGAGCGCCTA TACTTAACGT TCATCCCGTG AAATAAGGAA TCT | 643 |

(2) INFORMATION FOR SEQ ID NO:22:

(i) SEQUENCE CHARACTERISTICS:
        (A) LENGTH: 1348 base pairs
        (B) TYPE: nucleic acid
        (C) STRANDEDNESS: double
        (D) TOPOLOGY: linear (xi) SEQUENCE DESCRIPTION: SEQ ID NO:22:

| | | |
|---|---|---|
| AGACCAGCCT GTGGGTTTT TATTTCTGTT GTAGAGAGTT GAGTTCATGG | 50 |
| AATCCCTGAC GTTACAACCC ATCGCTCGTG TCGATGGCAC TATTAATCTG | 100 |
| CCCGGTTCCA AGACCGTTTC TAACCGCGCT TTATTGCTGG CGGCATTAGC | 150 |
| ACACGGCAAA ACAGTATTAA CCAATCTGCT GGATAGCGAT GACGTGCGCC | 200 |
| ATATGCTGAA TGCATTAACA GCGTTAGGGG TAAGCTATAC GCTTTCAGCC | 250 |
| GATCGTACGC GTTGCGAAAT TATCGGTAAC GGCGGTCCAT TACACGCAGA | 300 |
| AGGTGCCCTG GAGTTGTTCC TCGGTAACGC CGGAACGGCA ATGCGTCCGC | 350 |
| TGGCGGCAGC TCTTTGTCTG GGTAGCAATG ATATTGTGCT GACCGGTGAG | 400 |
| CCGCGTATGA AGAACGCCC GATTGGTCAT CTGGTGGATG CGCTGCGCCT | 450 |
| GGGCGGGGCG AAGATCACTT ACCTGGAACA AGAAAATTAT CCGCCGTTGC | 500 |
| GTTTACAGGG CGGCTTTACT GGCGGCAACG TTGACGTTGA TGGCTCCGTT | 550 |
| TCCAGCCAAT TCCTCACCGC ACTGTTAATG ACTGCGCCTC TTGCGCCGGA | 600 |
| AGATACGGTG ATTCGTATTA AAGGCGATCT GGTTTCTAAA CCTTATATCG | 650 |
| ACATCACACT CAATCTGATG AAGACGTTTG GTGTTGAAAT TGAAAATCAG | 700 |
| CACTATCAAC AATTTGTCGT AAAAGGCGGG CAGTCTTATC AGTCTCCGGG | 750 |
| TACTTATTTG GTCGAAGGCG ATGCATCTTC GGCTTCTTAC TTTCTGGCAG | 800 |
| CAGCAGCAAT CAAAGGCGGC ACTGTAAAAG TGACCGGTAT TGGACGTAAC | 850 |

| | |
|---|---:|
| AGTATGCAGG GTGATATTCG CTTTGCTGAT GTGCTGGAAA AAATGGGCGC | 900 |
| GACCATTTGC TGGGGCGATG ATTATATTTC CTGCACGCGT GGTGAACTGA | 950 |
| ACGCTATTGA TATGGATATG AACCATATTC CTGATGCGGC GATGACCATT | 1000 |
| GCCACGGCGG CGTTATTTGC AAAAGGCACC ACCAGGCTGC GCAATATCTA | 1050 |
| TAACTGGCGT GTTAAAGAGA CCGATCGCCT GTTTGCGATG CAACAGAAC | 1100 |
| TGCGTAAAGT CGGCGCGGAA GTGGAAGAGG GGCACGATTA CATTCGTATC | 1150 |
| ACTCCTCCGG AAAAACTGAA CTTTGCCGAG ATCGCGACAT ACAATGATCA | 1200 |
| CCGGATGGCG ATGTGTTTCT CGCTGGTGGC GTTGTCAGAT ACACCAGTGA | 1250 |
| CGATTCTTGA TCCCAAATGC ACGGCCAAAA CATTTCCGGA TTATTTCGAG | 1300 |
| CAGCTGGCGC GGATTAGCCA GGCAGCCTGA ATGAACAACG GGCAAGGT | 1348 |

(2) INFORMATION FOR SEQ ID NO:23:

(i) SEQUENCE CHARACTERISTICS:
        (A) LENGTH: 1300 base pairs
        (B) TYPE: nucleic acid
        (C) STRANDEDNESS: double
        (D) TOPOLOGY: linear (xi) SEQUENCE DESCRIPTION: SEQ ID NO:23:

| | |
|---|---:|
| ACCGTTGGCC AATGAACGAA TCCGCTGTAT GAAGAGATTG CCGACGTGAC | 50 |
| CATTCGTACT GATGATCAAA GCGCTAAAGT GGTTGCAAAC CAGATTATTC | 100 |
| ACATGCTGGA AAGCAACTAA TTCTGGCTTT ATATACACTC GTCTGCGGGT | 150 |
| ACAGTAATTA AGGTGGATGT CGCGTTATGG AGAGGATTGC CGTTACTCTC | 200 |
| GGGGAACGTA GTTACCCAAT TACCATCGCA TCTGGTTTGT TTAATGAACC | 250 |
| AGCTTCATTC TTACCGCTGA AATCGGGCGA GCAGGTCATG TTGGTCACCA | 300 |
| ACGAAACCCT GGCTCCTCTG TATCTCGATA AGGTCCGCGG CGTACTTGAA | 350 |
| CAGGCGGGTG TTAACGTCGA TAGCGTTATC CTCCCTGACG GCGAGCAGTA | 400 |
| TAAAAGCCTG GCTGTACTCG ATACCGTCTT TACGGCGTTG TTACAAAAAC | 450 |
| CGCATGGTCG CGATACTACG CTGGTGGCGC TTGGCGGCGG CGTAGTGGGC | 500 |
| GATCTGACCG GCTTCGCGGC GGCGAGTTAT CAGCGCGGTG TCCGTTTCAT | 550 |
| TCAAGTCCCG ACGACGTTAC TGTCGCAGGT CGATTCCTCC GTTGGCGGCA | 600 |
| AAACTGCGGT CAACCATCCC CTCGGTAAAA ACATGATTGG CGCGTTCTAC | 650 |
| CAACCTGCTT CAGTGGTGGT GGATCTCGAC TGTCTGAAAA CGCTTCCCCC | 700 |
| GCGTGAGTTA GCGTCGGGGC TGGCAGAAGT CATCAAATAC GGCATTATTC | 750 |
| TTGACGGTGC GTTTTTTAAC TGGCTGGAAG AGAATCTGGA TGCGTTGTTG | 800 |
| CGTCTGGACG GTCCGGCAAT GGCGTACTGT ATTCGCCGTT GTTGTGAACT | 850 |
| GAAGGCAGAA GTTGTCGCCG CCGACGAGCG CGAAACCGGG TTACGTGCTT | 900 |
| TACTGAATCT GGGACACACC TTTGGTCATG CCATTGAAGC TGAAATGGGG | 950 |
| TATGGCAATT GGTTACATGG TGAAGCGGTC GCTGCGGGTA TGGTGATGGC | 1000 |
| GGCGCGGACG TCGAACGTC TCGGGCAGTT TAGTTCTGCC GAAACGCAGC | 1050 |
| GTATTATAAC CCTGCTCAAG CGGGCTGGGT TACCGGTCAA TGGGCCGCGC | 1100 |
| GAAATGTCCG CGCAGGCGTA TTTACCGCAT ATGCTGCGTG ACAAGAAAGT | 1150 |
| CCTTGCGGGA GAGATGCGCT TAATTCTTCC GTTGGCAATT GGTAAGAGTG | 1200 |

| | |
|---|---|
| AAGTTCGCAG CGGCGTTTCG CACGAGCTTG TTCTTAACGC CATTGCCGAT | 1250 |
| TGTCAATCAG CGTAACAACA AGAAAGGTCA GGCCGCTTAT CAAGGAATTC | 1300 |

(2) INFORMATION FOR SEQ ID NO:24:

(i) SEQUENCE CHARACTERISTICS:
        (A) LENGTH: 854 base pairs
        (B) TYPE: nucleic acid
        (C) STRANDEDNESS: double
        (D) TOPOLOGY: linear (xi) SEQUENCE DESCRIPTION: SEQ ID NO:24:

| | |
|---|---|
| AAGCTTCTTT TCAGCTCCAA ATCTCATGGT AAATATGCGC TTTTCCCCAT | 50 |
| TTTTACTGCG AGTTGGCGAG CTCATCGTAT AATGAATAAG GGTGTTTAAG | 100 |
| TAAAGGAAAA CATCACCGTT CCTGGCATCC TGGACGGTGA TGCCCTACGG | 150 |
| TTGCCCTCGC CAGCACGGGC ATCGGTAAAG CGTAAGGTTC AACATCGTTT | 200 |
| TACCACTTCA TGCGATTGTT GCGTTTTTGT TGCGTATTAG ATCACTTAAT | 250 |
| TTGCTTTACA TCTCCCGTAA ACACTTTTCT GCGATACAAT GCCTTTACGT | 300 |
| TATGTAACGG AGAGTTCGGC ATGTCACACC CCGCGTTAAC GCAACTGCGT | 350 |
| GCGCTGCGCT ATTGTAAAGA GATCCCTGCC CTGGATCCGC AACTGCTCGA | 400 |
| CTGGCTGTTG CTGGAGGATT CCATGACAAA ACGTTTTGAA CAGCAGGAA | 450 |
| AAACGGTAAG CGTGACGATG ATCCGCGAAG GGTTTGTCGA GCAGAATGAA | 500 |
| ATCCCCGAAG AACTGCCGCT GCTGCCGAAA GAGTCTCGTT ACTGGTTACG | 550 |
| TGAAATTTTG TTATGTGCCG ATGGTGAACC GTGGCTTGCC GGTCGTACCG | 600 |
| TCGTTCCTGT GTCAACGTTA AGCGGGCCGG AGCTGGCGTT ACAAAAATTG | 650 |
| GGTAAAACGC CGTTAGGACG CTATCTGTTC ACATCATCGA CATTAACCCG | 700 |
| GGACTTTATT GAGATAGGCC GTGATGCCGG GCTGTGGGGG CGACGTTCCC | 750 |
| GCCTGCGATT AAGCGGTAAA CCGCTGTTGC TAACAGAACT GTTTTTACCG | 800 |
| GCGTCACCGT TGTACTAAGA GGAAAAAAAT ATGGAGTGGA GTCTGACGCA | 850 |
| GCTG | 854 |

(2) INFORMATION FOR SEQ ID NO:25:

(i) SEQUENCE CHARACTERISTICS:
        (A) LENGTH: 6641 base pairs
        (B) TYPE: nucleic acid
        (C) STRANDEDNESS: double
        (D) TOPOLOGY: linear (xi) SEQUENCE DESCRIPTION: SEQ ID NO:25:

| | |
|---|---|
| AAGCTTCTTT TCAGCTCCAA ATCTCATGGT AAATATGCGC TTTTCCCCAT | 50 |
| TTTTACTGCG AGTTGGCGAG CTCATCGTAT AATGAATAAG GGTGTTTAAG | 100 |
| TAAAGGAAAA CATCACCGTT CCTGGCATCC TGGACGGTGA TGCCCTACGG | 150 |
| TTGCCCTCGC CAGCACGGGC ATCGGTAAAG CGTAAGGTTC AACATCGTTT | 200 |
| TACCACTTCA TGCGATTGTT GCGTTTTTGT TGCGTATTAG ATCACTTAAT | 250 |
| TTGCTTTACA TCTCCCGTAA ACACTTTTCT GCGATACAAT GCCTTTACGT | 300 |
| TATGTAACGG AGAGTTCGGC ATGTCACACC CCGCGTTAAC GCAACTGCGT | 350 |
| GCGCTGCGCT ATTGTAAAGA GATCCCTGCC CTGGATCCGC AACTGCTCGA | 400 |

-continued

| | |
|---|---|
| CTGGCTGTTG CTGGAGGATT CCATGACAAA ACGTTTTGAA CAGCAGGGAA | 450 |
| AAACGGTAAG CGTGACGATG ATCCGCGAAG GGTTTGTCGA GCAGAATGAA | 500 |
| ATCCCCGAAG AACTGCCGCT GCTGCCGAAA GAGTCTCGTT ACTGGTTACG | 550 |
| TGAAATTTTG TTATGTGCCG ATGGTGAACC GTGGCTTGCC GGTCGTACCG | 600 |
| TCGTTCCTGT GTCAACGTTA AGCGGGCCGG AGCTGGCGTT ACAAAAATTG | 650 |
| GGTAAAACGC CGTTAGGACG CTATCTGTTC ACATCATCGA CATTAACCCG | 700 |
| GGACTTTATT GAGATAGGCC GTGATGCCGG GCTGTGGGGG CGACGTTCCC | 750 |
| GCCTGCGATT AAGCGGTAAA CCGCTGTTGC TAACAGAACT GTTTTTACCG | 800 |
| GCGTCACCGT TGTACTAAGA GGAAAAAAAT ATGGAGTGGA GTCTGACGCA | 850 |
| GCTGCAGGTC GACACCCCGT TTACACATTC TGACGGAAGA TATAGATTGG | 900 |
| AAGTATTGCA TTCACTAAGA TAAGTATGGC AACACTGGAA CAGACATGAA | 950 |
| TTATCAGAAC GACGATTTAC GCATCAAAGA AATCAAAGAG TTACTTCCTC | 1000 |
| CTGTCGCATT GCTGGAAAAA TTCCCCGCTA CTGAAAATGC CGCGAATACG | 1050 |
| GTTGCCCATG CCCGAAAAGC GATCCATAAG ATCCTGAAAG GTAATGATGA | 1100 |
| TCGCCTGTTG GTTGTGATTG GCCCATGCTC AATTCATGAT CCTGTCGCGG | 1150 |
| CAAAAGAGTA TGCCACTCGC TTGCTGGCGC TGCGTGAAGA GCTGAAAGAT | 1200 |
| GAGCTGGAAA TCGTAATGCG CGTCTATTTT GAAAAGCCGC GTACCACGGT | 1250 |
| GGGCTGGAAA GGGCTGATTA ACGATCCGCA TATGGATAAT AGCTTCCAGA | 1300 |
| TCAACGACGG TCTGCGTATA GCCCGTAAAT TGCTGCTTGA TATTAACGAC | 1350 |
| AGCGGTCTGC CAGCGGCAGG TGAGTTTCTC GATATGATCA CCCCACAATA | 1400 |
| TCTCGCTGAC CTGATGAGCT GGGGCGCAAT TGGCGCACGT ACCACCGAAT | 1450 |
| CGCAGGTGCA CCGCGAACTG GCATCAGGGC TTTCTTGTCC GGTCGGCTTC | 1500 |
| AAAAATGGCA CCGACGGTAC GATTAAAGTG GCTATCGATG CCATTAATGC | 1550 |
| CGCCGGTGCG CCGCACTGCT TCCTGTCCGT AACGAAATGG GGGCATTCGG | 1600 |
| CGATTGTGAA TACCAGCGGT AACGGCGATT GCCATATCAT TCTGCGCGGC | 1650 |
| GGTAAAGAGC CTAACTACAG CGCGAAGCAC GTTGCTGAAG TGAAAGAAGG | 1700 |
| GCTGAACAAA GCAGGCCTGC CAGCACAGGT GATGATCGAT TTCAGCCATG | 1750 |
| CTAACTCGTC CAAACAATTC AAAAAGCAGA TGGATGTTTG TGCTGACGTT | 1800 |
| TGCCAGCAGA TTGCCGGTGG CGAAAAGGCC ATTATTGGCG TGATGGTGGA | 1850 |
| AAGCCATCTG GTGGAAGGCA ATCAGAGCCT CGAGAGCGGG GAGCCGCTGG | 1900 |
| CCTACGGTAA GAGCATCACC GATGCCTGCA TCGGCTGGGA AGATACCGAT | 1950 |
| GCTCTGTTAC GTCAACTGGC GAATGCAGTA AAAGCGCGTC GCGGGTAAGG | 2000 |
| TTTAATTGTC GGATGCGCCG TCAGAGTGGC GTATCCGATG GATCCTCCCG | 2050 |
| GCGTAGCCCA AAACGCGCTG TCGTCAAGTC GTTAAGGGCG TGCCCTTCAT | 2100 |
| CATCCGATCT GGAGTCAAAA TGTCCTCACG TAAAGAGCTT GCCAATGCTA | 2150 |
| TTCGTGCGCT GAGCATGGAC GCAGTACAGA AGCCAAATC CGGTCACCCG | 2200 |
| GGGGCCCCTA TGGGTATGGC TGACATTGCC GAAGTCCTGT GGCGTGATTT | 2250 |
| CCTGAAACAC AACCCGCAGA ATCCGTCCTG GGCTGACCGT GACCGCTTCG | 2300 |
| TGCTGTCCAA CGGCCACGGC TCCATGCTGA TCTACAGCCT GCTGCACCTC | 2350 |
| ACCGGTTACG ATCTGCCGAT GGAAGAACTG AAAAACTTCC GTCAGCTGCA | 2400 |

| | |
|---|---|
| CTCTAAAACT CCGGGTCACC CGGAAAGTGG GGTTACACCG CTGGGTGTGG | 2450 |
| AAACCACCAC CGGTCCGCTG GGTCAGGGTA TTGCCAACGC AGTCGGTATG | 2500 |
| GCGATTGCAG AAAAAACGCT GGCGGCGCAG TTTAACCGTC CGGGCCACGA | 2550 |
| CATTGTCGAC CACTACACCT ACGCCTTCAT GGGCGACGGC TGCATGATGG | 2600 |
| AAGGCATCTC CCACGAAGTT TGCTCTCTGG CGGGTACGCT GAAGCTGGGT | 2650 |
| AAACTGATTG CATTCTACGA TGACAACGGT ATTTCTATCG ATGGTCACGT | 2700 |
| TGAAGGCTGG TTCACCGACG ACACCGCAAT GCGTTTCGAA GCTTACGGCT | 2750 |
| GGCACGTTAT TCGCGACATC GACGGTCATG ACGCGGCATC TATCAAACGC | 2800 |
| GCAGTAGAAG AAGCGCGCGC AGTGACTGAC AAACCTTCCC TGCTGATGTG | 2850 |
| CAAAACCATC ATCGGTTTCG GTTCCCCGAA CAAAGCCGGT ACCCACGACT | 2900 |
| CCCACGGTGC GCCGCTGGGC GACGCTGAAA TTGCCCTGAC CCGCGAACAA | 2950 |
| CTGGGCTGGA AATATGCGCC GTTCGAAATC CCGTCTGAAA TCTATGCTCA | 3000 |
| GTGGGATGCG AAAGAAGCAG GCCAGGCGAA AGAATCCGCA TGGAACGAGA | 3050 |
| AATTCGCTGC TTACGCGAAA GCTTATCCGC AGGAAGCCGC TGAATTTACC | 3100 |
| CGCCGTATGA AGGCGAAAT GCCGTCTGAC TTCGACGCTA AAGCGAAAGA | 3150 |
| GTTCATCGCT AAACTGCAGG CTAATCCGGC GAAAATCGCC AGCCGTAAAG | 3200 |
| CGTCTCAGAA TGCTATCGAA GCGTTCGGTC CGCTGTTGCC GGAATTCCTC | 3250 |
| GGCGGTTCTG CTGACCTGGC GCCGTCTAAC CTGACCCTGT GGTCTGGTTC | 3300 |
| TAAAGCAATC AACGAAGATG CTGCGGGTAA CTACATCCAC TACGGTGTTC | 3350 |
| GCGAGTTCGG TATGACCGCG ATTGCTAACG GTATCTCCCT GCACGGTGGC | 3400 |
| TTCCTGCCGT ACACCTCCAC CTTCCTGATG TTCGTGGAAT ACGCACGTAA | 3450 |
| CGCCGTACGT ATGGCTGCGC TGATGAAACA GCGTCAGGTG ATGGTTTACA | 3500 |
| CCCACGACTC CATCGGTCTG GGCGAAGACG GGCCGACTCA CCAGCCGGTT | 3550 |
| GAGCAGGTCG CTTCTCTGCG CGTAACCCCG AACATGTCTA CATGGCGTCC | 3600 |
| GTGTGACCAG GTTGAATCCG CGGTCGCGTG GAAATACGGT GTTGAGCGTC | 3650 |
| AGGACGGCCC GACCGCACTG ATCCTCTCCC GTCAGAACCT GGCGCAGCAG | 3700 |
| GAACGAACTG AAGAGCAACT GGCAAACATC GCGCGCGGTG GTTATGTGCT | 3750 |
| GAAAGACTGC GCCGGTCAGC CGGAACTGAT TTTCATCGCT ACCGGTTCAG | 3800 |
| AAGTTGAACT GGCTGTTGCT GCCTACGAAA AACTGACTGC CGAAGGCGTG | 3850 |
| AAAGCGCGCG TGGTGTCCAT GTCGTCTACC GACGCATTTG ACAAGCAGGA | 3900 |
| TGCTGCTTAC CGTGAATCCG TACTGCCGAA AGCGGTTACT GCACGCGTTG | 3950 |
| CTGTAGAAGC GGGTATTGCT GACTACTGGT ACAAGTATGT TGGCCTGAAC | 4000 |
| GGTGCTATCG TCGGTATGAC CACCTTCGGT GAATCTGCTC CGGCAGAGCT | 4050 |
| GCTGTTTGAA GAGTTCGGCT TCACTGTTGA TAACGTTGTT GCGAAAGCAA | 4100 |
| AGAACTGCT GTAATTAGCA TTTCGGGTAA AAAGGTCGC TTCGGCGACC | 4150 |
| TTTTTTATTA CCTTGATAAT GTCCGTTTGC GGGAGCTCAA ATGCGCAGAA | 4200 |
| ATGTGTTTCT CAAACCGTTC ATTTATCACA AAAGGATTGT TCGATGTCCA | 4250 |
| ACAATGGCTC GTCACCGCTG GTGCTTTGGT ATAACCAACT CGGCATGAAT | 4300 |
| GATGTAGACA GGGTTGGGGG CAAAAATGCC TCCCTGGGTG AAATGATTAC | 4350 |

```
TAATCTTTCC GGAATGGGTG TTTCCGTTCC GAATGGTTTC GCCACAACCG        4400

CCGACGCGTT TAACCAGTTT CTGGACCAAA GCGGCGTAAA CCAGCGCATT        4450

TATGAACTGC TGGATAAAAC GGATATTGAC GATGTTACTC AGCTTGCGAA        4500

AGCGGGCGCG CAAATCCGCC AGTGGATTAT CGACACTCCC TTCCAGCCTG        4550

AGCTGGAAAA CGCCATCCGC GAAGCCTATG CACAGCTTTC CGCCGATGAC        4600

GAAAACGCCT CTTTTGCGGT GCGCTCCTCC GCCACCGCAG AAGATATGCC        4650

GGACGCTTCT TTTGCCGGTC AGCAGGAAAC CTTCCTCAAC GTTCAGGGTT        4700

TTGACGCCGT TCTCGTGGCA GTGAAACATG TATTTGCTTC TCTGTTTAAC        4750

GATCGCGCCA TCTCTTATCG TGTGCACCAG GGTTACGATC ACCGTGGTGT        4800

GGCGCTCTCC GCCGGTGTTC AACGGATGGT GCGCTCTGAC CTCGCATCAT        4850

CTGGCGTGAT GTTCTCCATT GATACCGAAT CCGGCTTTGA CCAGGTGGTG        4900

TTTATCACTT CCGCATGGGG CCTTGGTGAG ATGGTCGTGC AGGGTGCGGT        4950

TAACCCGGAT GAGTTTTACG TGCATAAACC GACACTGGCG GCGAATCGCC        5000

CGGCTATCGT GCGCCGCACC ATGGGGTCGA AAAAAATCCG CATGGTTTAC        5050

GCGCCGACCC AGGAGCACGG CAAGCAGGTT AAAATCGAAG ACGTACCGCA        5100

GGAACAGCGT GACATCTTCT CGCTGACCAA CGAAGAAGTG CAGGAACTGG        5150

CAAAACAGGC CGTACAAATT GAGAAACACT ACGGTCGCCC GATGGATATT        5200

GAGTGGGCGA AAGATGGCCA CACCGGTAAA CTGTTCATTG TGCAGGCGCG        5250

TCCGGAAACC GTGCGCTCAC GCGGTCAGGT CATGGAGCGT TATACGCTGC        5300

ATTCACAGGG TAAGATTATC GCCGAAGGCC GTGCTATCGG TCATCGCATC        5350

GGTGCGGGTC CGGTGAAAGT CATCCATGAC ATCAGCGAAA TGAACCGCAT        5400

CGAACCTGGC GACGTGCTGG TTACTGACAT GACCGACCCG GACTGGGAAC        5450

CGATCATGAA GAAAGCATCT GCCATCGTCA CCAACCGTGG CGGTCGTACC        5500

TGTCACGCGG CGATCATCGC TCGTGAACTG GGCATTCCGG CGGTAGTGGG        5550

CTGTGGAGAT GCAACAGAAC GGATGAAAGA CGGTGAGAAC GTCACTGTTT        5600

CTTGTGCCGA AGGTGATACC GGTTACGTCT ATGCGGAGTT GCTGGAATTT        5650

AGCGTGAAAA GCTCCAGCGT AGAAACGATG CCGGATCTGC CGTTGAAAGT        5700

GATGATGAAC GTCGGTAACC CGGACCGTGC TTTCGACTTC GCCTGCCTAC        5750

CGAACGAAGG CGTGGGCCTT GCGCGTCTGG AATTTATCAT CAACCGTATG        5800

ATTGGCGTCC ACCCACGCGC ACTGCTTGAG TTTGACGATC AGGAACCGCA        5850

GTTGCAAAAC GAAATCCGCG AGATGATGAA AGGTTTTGAT TCTCCGCGTG        5900

AATTTTACGT TGGTCGTCTG ACTGAAGGGA TCGCGACGCT GGGTGCCGCG        5950

TTTTATCCGA AGCGCGTCAT TGTCCGTCTC TCTGATTTTA AATCGAACGA        6000

ATATGCCAAC CTGGTCGGTG GTGAGCGTTA CGAGCCAGAT GAAGAGAACC        6050

CGATGCTCGG CTTCCGTGGC GCGGGCCGCT ATGTTTCCGA CAGCTTCCGC        6100

GACTGTTTCG CGCTGGAGTG TGAAGCAGTG AAACGTGTGC GCAACGACAT        6150

GGGACTGACC AACGTTGAGA TCATGATCCC GTTCGTGCGT ACCGTAGATC        6200

AGGCGAAAGC GGTGGTTGAA GAACTGGCGC GTCAGGGGCT GAAACGTGGC        6250

GAGAACGGGC TGAAAATCAT CATGATGTGT GAAATCCCGT CCAACGCCTT        6300

GCTGGCCGAG CAGTTCCTCG AATATTTCGA CGGCTTCTCA ATTGGCTCAA        6350
```

| | |
|---|---|
| ACGATATGAC GCAGCTGGCG CTCGGTCTGG ACCGTGACTC CGGCGTGGTG | 6400 |
| TCTGAATTGT TCGATGAGCG CAACGATGCG GTGAAAGCAC TGCTGTCGAT | 6450 |
| GGCTATCCGT GCCGCGAAGA AACAGGGCAA ATATGTCGGG ATTTGCGGTC | 6500 |
| AGGGTCCGTC CGACCACGAA GACTTTGCCG CATGGTTGAT GGAAGAGGGG | 6550 |
| ATCGATAGCC TGTCTCTGAA CCCGGACACC GTGGTGCAAA CCTGGTTAAG | 6600 |
| CCTGGCTGAA CTGAAGAAAT AAAATAAATC CCCGGGAATT C | 6641 |

(2) INFORMATION FOR SEQ ID NO:26:

(i) SEQUENCE CHARACTERISTICS:
  (A) LENGTH: 4530 base pairs
  (B) TYPE: nucleic acid
  (C) STRANDEDNESS: double
  (D) TOPOLOGY: linear (xi) SEQUENCE DESCRIPTION: SEQ ID NO:26:

| | |
|---|---|
| AAGCTTATAA CGGCGGCGAT GGTGTGTTTA TGCTCACCAA AGAGCAGCTT | 50 |
| ATTGCCGCAC GAGAACATTT CGCGATTTAT AAAGATTAAG TAAACACGCA | 100 |
| AACACAACAA TAACGGAGCC GTGATGGCTG GAAACACAAT TGGACAACTC | 150 |
| TTTCGCGTAA CCACCTTCGG CGAATCGCAC GGGCTGGCGC TCGGCTGCAT | 200 |
| CGTCGATGGT GTTCCGCCAG GCATTCCGCT GACGGAAGCG GACCTGCAAC | 250 |
| ATGACCTCGA CCGTCGTCGC CCTGGGACAT CGCGCTATAC CACCCAGCGC | 300 |
| CGCGAGCCGG ATCAGGTCAA AATTCTCTCC GGTGTTTTTG AAGGCGTTAC | 350 |
| TACCGGCACC AGCATTGGCT TGTTGATCGA AAACACTGAC CAGCGCTCTC | 400 |
| AGGATTACAG TGCGATTAAG GACGTTTTCC GTCCAGGCCA TGCCGATTAC | 450 |
| ACCTACGAAC AAAAATACGG TCTGCGCGAT TATCGCGGCG GTGGACGTTC | 500 |
| TTCCGCCCGC GAAACCGCCA TGCGCGTGGC GGCAGGAGCT ATTGCCAAAA | 550 |
| AATATCTCGC CGAGAAATTT GGTATTGAAA TCCGTGGCTG CCTGACCCAG | 600 |
| ATGGGCGACA TTCCGCTGGA TATCAAAGAC TGGTCGCAGG TCGAGCAAAA | 650 |
| TCCGTTTTTT TGCCCGGACC CCGACAAAAT CGACGCGTTA GACGAGTTGA | 700 |
| TGCGTGCGCT GAAAAAAGAG GGCGACTCCA TCGGCGCTAA AGTCACCGTT | 750 |
| GTTGCCAGTG GCGTTCCTGC CGGACTTGGC GAGCCGGTCT TTGACCGCCT | 800 |
| GGATGCTGAC ATCGCCCATG CGCTGATGAG CATCAACGCG GTGAAAGGCG | 850 |
| TGGAAATTGG CGACGGCTTT GACGTGGTGG CGCTGCGCGG CAGCCAGAAC | 900 |
| CGCGATGAAA TCACCAAAGA CGGTTTCCAG AGCAACCATG CGGGCGGCAT | 950 |
| TCTCGGCGGT ATCAGCAGCG GGCAGCAAAT CATTGCCCAT ATGGCGCTGA | 1000 |
| AACCGACCTC CAGCATTACC GTGCCGGGTC GTACCATTAA CCGCTTTGGC | 1050 |
| GAAGAAGTTG AGATGATCAC CAAAGGCCGT CACGATCCCT GTGTCGGGAT | 1100 |
| CCGCGCAGTG CCGATCGCAG AAGCGAATGC TGGCGATCGT TTTAATGGAT | 1150 |
| CACCTGTTAC GGCAACGGGC GCAAAATGCC GATGTGAAGA CTGATATTCC | 1200 |
| ACGCTGGTAA AAAATGAATA AAACCGCGAT TGCGCTCTGC AGTGATGGTA | 1250 |
| TGATCGCTAT TCTCATGACA CCGGCTTTCG CGCATTGCGA CCTATTGGGG | 1300 |
| AAAACCCACG ATGACACAAC CTCTTTTTCT GATCGGGCCT CGGGGCTGTG | 1350 |
| GTAAAACAAC GGTCGGAATG GCCCTTGCCG ATTCGCTTAA CCGTCGGTTT | 1400 |

-continued

```
GTCGATACCG ATCAGTGGTT GCAATCACAG CTCAATATGA CGGTCGCGGA      1450

GATCGTCGAA AGGGAAGAGT GGGCGGGATT TCGCGCCAGA GAAACGGCGG      1500

CGCTGGAAGC GGTAACTGCG CCATCCACCG TTATCGCTAC AGGCGGCGGC      1550

ATTATTCTGA CGGAATTTAA TCGTCACTTC ATGCAAAATA ACGGGATCGT      1600

GGTTTATTTG TGTGCGCCAG TATCAGTCCT GGTTAACCGA CTGCAAGCTG      1650

CACCGGAAGA AGATTTACGG CCAACCTTAA CGGGAAAACC GCTGAGCGAA      1700

GAAGTTCAGG AAGTGCTGGA AGAACGCGAT GCGCTATATC GCGAAGTTGC      1750

GCATATTATC ATCGACGCAA CAAACGAACC CAGCCAGGTG ATTTCTGAAA      1800

TTCGCAGCGC CCTGGCACAG ACGATCAATT GTTGATTTTC GAGCGCCTAT      1850

ACTTAACGTT CATCCCGTGA AATAAGGAAT CTAGACCAGC CTGTGGGGTT      1900

TTTATTTCTG TTGTAGAGAG TTGAGTTCAT GGAATCCCTG ACGTTACAAC      1950

CCATCGCTCG TGTCGATGGC ACTATTAATC TGCCCGGTTC CAAGACCGTT      2000

TCTAACCGCG CTTTATTGCT GGCGGCATTA GCACACGGCA AAACAGTATT      2050

AACCAATCTG CTGGATAGCG ATGACGTGCG CCATATGCTG AATGCATTAA      2100

CAGCGTTAGG GGTAAGCTAT ACGCTTTCAG CCGATCGTAC GCGTTGCGAA      2150

ATTATCGGTA ACGGCGGTCC ATTACACGCA GAAGGTGCCC TGGAGTTGTT      2200

CCTCGGTAAC GCCGGAACGG CAATGCGTCC GCTGGCGGCA GCTCTTTGTC      2250

TGGGTAGCAA TGATATTGTG CTGACCGGTG AGCCGCGTAT GAAAGAACGC      2300

CCGATTGGTC ATCTGGTGGA TGCGCTGCGC CTGGGCGGGG CGAAGATCAC      2350

TTACCTGGAA CAAGAAAATT ATCCGCCGTT GCGTTTACAG GGCGGCTTTA      2400

CTGGCGGCAA CGTTGACGTT GATGGCTCCG TTTCCAGCCA ATTCCTCACC      2450

GCACTGTTAA TGACTGCGCC TCTTGCGCCG GAAGATACGG TGATTCGTAT      2500

TAAAGGCGAT CTGGTTTCTA AACCTTATAT CGACATCACA CTCAATCTGA      2550

TGAAGACGTT TGGTGTTGAA ATTGAAAATC AGCACTATCA ACAATTTGTC      2600

GTAAAAGGCG GGCAGTCTTA TCAGTCTCCG GGTACTTATT TGGTCGAAGG      2650

CGATGCATCT TCGGCTTCTT ACTTTCTGGC AGCAGCAGCA ATCAAAGGCG      2700

GCACTGTAAA AGTGACCGGT ATTGGACGTA ACAGTATGCA GGGTGATATT      2750

CGCTTTGCTG ATGTGCTGGA AAAAATGGGC GCGACCATTT GCTGGGGCGA      2800

TGATTATATT TCCTGCACGC GTGGTGAACT GAACGCTATT GATATGGATA      2850

TGAACCATAT TCCTGATGCG GCGATGACCA TTGCCACGGC GGCGTTATTT      2900

GCAAAGGCA CCACCAGGCT GCGCAATATC TATAACTGGC GTGTTAAAGA      2950

GACCGATCGC CTGTTTGCGA TGGCAACAGA ACTGCGTAAA GTCGGCGCGG      3000

AAGTGGAAGA GGGGCACGAT TACATTCGTA TCACTCCTCC GGAAAAACTG      3050

AACTTTGCCG AGATCGCGAC ATACAATGAT CACCGGATGG CGATGTGTTT      3100

CTCGCTGGTG GCGTTGTCAG ATACACCAGT GACGATTCTT GATCCCAAAT      3150

GCACGGCCAA ACATTTCCG GATTATTTCG AGCAGCTGGC GCGGATTAGC      3200

CAGGCAGCCT GAATGAACAA CGGGCAAGGT ACCGTTGGCC AATGAACGAA      3250

TCCGCTGTAT GAAGAGATTG CCGACGTGAC CATTCGTACT GATGATCAAA      3300

GCGCTAAAGT GGTTGCAAAC CAGATTATTC ACATGCTGGA AAGCAACTAA      3350
```

-continued

| | | | | |
|---|---|---|---|---|
| TTCTGGCTTT | ATATACACTC | GTCTGCGGGT | ACAGTAATTA | AGGTGGATGT | 3400 |
| CGCGTTATGG | AGAGGATTGT | CGTTACTCTC | GGGGAACGTA | GTTACCCAAT | 3450 |
| TACCATCGCA | TCTGGTTTGT | TTAATGAACC | AGCTTCATTC | TTACCGCTGA | 3500 |
| AATCGGGCGA | GCAGGTCATG | TTGGTCACCA | ACGAAACCCT | GGCTCCTCTG | 3550 |
| TATCTCGATA | AGGTCCGCGG | CGTACTTGAA | CAGGCGGGTG | TTAACGTCGA | 3600 |
| TAGCGTTATC | CTCCCTGACG | GCGAGCAGTA | TAAAAGCCTG | GCTGTACTCG | 3650 |
| ATACCGTCTT | TACGGCGTTG | TTACAAAAAC | CGCATGGTCG | CGATACTACG | 3700 |
| CTGGTGGCGC | TTGGCGGCGG | CGTAGTGGGC | GATCTGACCG | GCTTCGCGGC | 3750 |
| GGCGAGTTAT | CAGCGCGGTG | TCCGTTTCAT | TCAAGTCCCG | ACGACGTTAC | 3800 |
| TGTCGCAGGT | CGATTCCTCC | GTTGGCGGCA | AAACTGCGGT | CAACCATCCC | 3850 |
| CTCGGTAAAA | ACATGATTGG | CGCGTTCTAC | CAACCTGCTT | CAGTGGTGGT | 3900 |
| GGATCTCGAC | TGTCTGAAAA | CGCTTCCCCC | GCGTGAGTTA | GCGTCGGGGC | 3950 |
| TGGCAGAAGT | CATCAAATAC | GGCATTATTC | TTGACGGTGC | GTTTTTTAAC | 4000 |
| TGGCTGGAAG | AGAATCTGGA | TGCGTTGTTG | CGTCTGGACG | GTCCGGCAAT | 4050 |
| GGCGTACTGT | ATTCGCCGTT | GTTGTGAACT | GAAGGCAGAA | GTTGTCGCCG | 4100 |
| CCGACGAGCG | CGAAACCGGG | TTACGTGCTT | TACTGAATCT | GGGACACACC | 4150 |
| TTTGGTCATG | CCATTGAAGC | TGAAATGGGG | TATGGCAATT | GGTTACATGG | 4200 |
| TGAAGCGGTC | GCTGCGGGTA | TGGTGATGGC | GGCGCGGACG | TCGGAACGTC | 4250 |
| TCGGGCAGTT | TAGTTCTGCC | GAAACGCAGC | GTATTATAAC | CCTGCTCAAG | 4300 |
| CGGGCTGGGT | TACCGGTCAA | TGGGCCGCGC | GAAATGTCCG | CGCAGGCGTA | 4350 |
| TTTACCGCAT | ATGCTGCGTG | ACAAGAAAGT | CCTTGCGGGA | GAGATGCGCT | 4400 |
| TAATTCTTCC | GTTGGCAATT | GGTAAGAGTG | AAGTTCGCAG | CGGCGTTTCG | 4450 |
| CACGAGCTTG | TTCTTAACGC | CATTGCCGAT | TGTCAATCAG | CGTAACAACA | 4500 |
| AGAAAGGTCA | GGCCGCTTAT | CAAGGAATTC | | | 4530 |